US009428460B2

(12) United States Patent
Nguyen et al.

(10) Patent No.: US 9,428,460 B2
(45) Date of Patent: Aug. 30, 2016

(54) *N*-[4-(QUINOLIN-4-YLOXY)CYCLOHEXYL(METHYL)](HETERO)ARYLCARBOX-AMIDES AS ANDROGEN RECEPTOR ANTAGONISTS, PRODUCTION AND USE THEREOF AS MEDICINAL PRODUCTS

(71) Applicant: BAYER PHARMA AKTIENGESELLSCHAFT, Berlin (DE)

(72) Inventors: Duy Nguyen, Berlin (DE); Hermann Künzer, Reinsfeld (DE); Hortensia Faus Gimenez, Berlin (DE); Benjamin Bader, Berlin (DE); Silke Köhr, Teltow (DE); Martin Fritsch, Berlin (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 14/408,876

(22) PCT Filed: Jun. 24, 2013

(86) PCT No.: PCT/EP2013/063118
§ 371 (c)(1),
(2) Date: Dec. 17, 2014

(87) PCT Pub. No.: WO2014/001247
PCT Pub. Date: Jan. 3, 2014

(65) Prior Publication Data
US 2015/0191431 A1    Jul. 9, 2015

(30) Foreign Application Priority Data

Jun. 26, 2012    (EP) .................................. 12004764

(51) Int. Cl.
| | |
|---|---|
| *C07D 215/233* | (2006.01) |
| *A61K 31/47* | (2006.01) |
| *C07D 401/12* | (2006.01) |
| *C07D 413/12* | (2006.01) |
| *A61K 31/4709* | (2006.01) |

(52) U.S. Cl.
CPC ........... *C07D 215/233* (2013.01); *A61K 31/47* (2013.01); *A61K 31/4709* (2013.01); *C07D 401/12* (2013.01); *C07D 413/12* (2013.01)

(58) Field of Classification Search
CPC ............. A61K 31/14; A61K 31/4709; C07D 215/233; C07D 401/12; C07D 413/12
See application file for complete search history.

(56) References Cited

U.S. PATENT DOCUMENTS

| | | | |
|---|---|---|---|
| 7,696,246 B2 | 4/2010 | Zhi et al. | |
| 7,858,623 B2 * | 12/2010 | Kim et al. | ............. 514/236.5 |
| 8,088,794 B2 * | 1/2012 | Kim et al. | .................... 514/312 |
| 8,685,983 B2 * | 4/2014 | Kim et al. | ............... 514/255.05 |
| 2003/0232854 A1 | 12/2003 | Bonjuklian et al. | |
| 2006/0293341 A1 | 12/2006 | Jubian et al. | |
| 2007/0185148 A1 | 8/2007 | Busch-Petersen et al. | |
| 2008/0312232 A1 | 12/2008 | Kim et al. | |
| 2009/0111864 A1 | 4/2009 | Jung et al. | |

FOREIGN PATENT DOCUMENTS

| | | |
|---|---|---|
| EP | 1550657 A1 | 7/2005 |
| EP | 1712235 A2 | 10/2006 |
| EP | 2088141 A2 | 8/2009 |
| WO | 2004/067516 A1 | 8/2004 |
| WO | 2005/030732 A1 | 4/2005 |
| WO | 2005/115972 A1 | 12/2005 |
| WO | 2005/117570 A1 | 12/2005 |
| WO | 2006/052722 A1 | 5/2006 |
| WO | 2006/116713 A1 | 11/2006 |
| WO | 2006/117552 A1 | 11/2006 |
| WO | 2006/117570 A1 | 11/2006 |
| WO | 2007/091694 A1 | 8/2007 |
| WO | 2007/146824 A2 | 12/2007 |
| WO | 2008/040934 A1 | 4/2008 |
| WO | 2008/064432 A1 | 6/2008 |
| WO | 2009/023655 A1 | 2/2009 |
| WO | 2009/140549 A1 | 11/2009 |
| WO | 2010/039248 A1 | 4/2010 |
| WO | 2011/011303 A1 | 1/2011 |
| WO | 2011/029782 A1 | 3/2011 |
| WO | 2012/009649 A1 | 1/2012 |

OTHER PUBLICATIONS

E J. Small, D. M. Reese, Curr. Opi. Oncol. 2000, 12, 265-272.
S. Leewansangtong, E. D. Crawford, Endocrine-Related Cancer 1998, 5, 325-339.
L. J. Denis, K. Griffith, Semin. in Surg. Onc. 2000, 18, 52-74.
D. J. Lamb et al. Vitam. Horm. 2001, 62, 199-230.
J. P. Elo, T. Visakorpi, Ann. Med. 2001, 33, 130-41.
Taplin et al., Cancer Res., 59: 2511-2515, 1999.
Veldscholte et al., Biochem. Biophys. Res. Commun., 173: 534-540, 1990.
Haapala et al., Lab. Invest., 81: 1647-1651, 2001.
Hara et al., Cancer Research, 63: 149-153, 2003.
Yoshida et al., Cancer Research, 65: 9611-9616, 2005.
Georget et al., Molecular Endocrinology, 20(4): 724-734, 2006.
P. Reid, P. Kantoff, W. Oh, Investigational New Drugs 1999, 17, 271-284.
J. Am. Chem. Soc. 1992, 114, 9327.
Org. Lett. 2011, 5048-5051.
Mitsunobu, O. Synthesis, 1981, 1-28.
Tet. Lett. 1998, 39. 2059-2062.
J. Org. Chem. 2005, 70, 1508-1510.
D Rachoń, Differential diagnosis of hyperandrogenism in women with polycystic ovary syndrome, Exp Clin Endocrinol Diabetes, 2012, 120(4): 205-209.

(Continued)

*Primary Examiner* — D M Seaman

(57) ABSTRACT

The invention relates to N-[4-(quinolin-4-yloxy)cyclohexyl(methyl)](hetero)arylcarboxamides, intermediates and methods for their production, use thereof for treating and/or preventing diseases and use thereof for producing medicinal products and use thereof for treating and/or preventing diseases, especially of hyperproliferative diseases.

23 Claims, 1 Drawing Sheet

(56) References Cited

OTHER PUBLICATIONS

Amsterdam ESHRE/ASRM-sponsored 3rd PCOS Consensus Workshop Group Consensus on women's health aspects of polycystic ovary syndrome (PCOS), Hum Reprod., 2012, 27(1): 14-24.

S. Yarak et al., Hyperandrogenism and skin: polycystic ovary syndrome and peripheral insulin resistance. An. Bras. Dermatol. [online] 2005, 80(4): 395-410.

Il Müderris et al., A comparison between two doses of flutamide (250 mg/d and 500 mg/d) in the treatment of hirsutism, Fertil Steril, 1997, 68(4): 644-7.

A Gambineri et al., Effect of flutamide and metformin administered alone or in combination in dieting obese women with polycystic ovary syndrome, Clin Endocrinol, 2004, 60: 241-249.

A Corbould, Chronic testosterone treatment induces selective insulin resistance in subcutaneous adipocytes of women, J Endocrinol, 2007, 192: 585-594.

J Brahm et al., Acute and fulminant hepatitis induced by flutamide: case series report and review of the literature, Ann Hepatol, 2011, 10(1): 93-8.

ID Cockshott et al., The pharmacokinetics of Casodex in prostate cancer patients after single and during multiple dosing, Eur Urol, 1990, 18 Suppl 3: 10-17.

HM Scott et al., Steroidogenesis in the fetal testis and its susceptibility to disruption by exogenous compounds, Endocr Rev, 2009, 30(7): 883-925.

\* cited by examiner

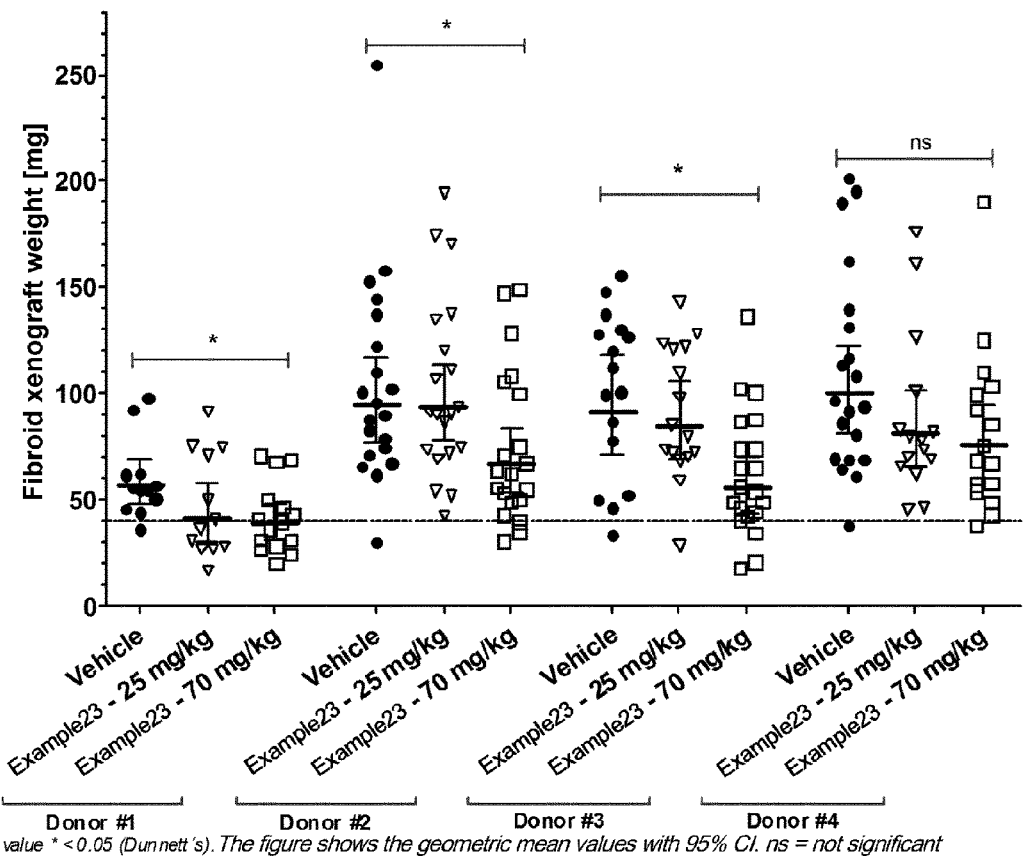

N-[4-(QUINOLIN-4-YLOXY)CYCLOHEXYL (METHYL)](HETERO)ARYLCARBOX-AMIDES AS ANDROGEN RECEPTOR ANTAGONISTS, PRODUCTION AND USE THEREOF AS MEDICINAL PRODUCTS

The invention relates to N-[4-(quinolin-4-yloxy)cyclohexyl(methyl)](hetero)arylcarboxamides, intermediates and methods of production thereof, use thereof for treating and/or preventing diseases and use thereof for producing medicinal products and use of the latter for treating and/or preventing diseases, especially hyperproliferative diseases.

In the industrial countries, prostatic carcinoma is, after lung cancer, the second main cause of death from cancer in men. In men over 55 years, 4% of deaths can be attributed to a prostate tumour disease and it is presumed that in men over 80 years the proportion rises to 70% of deaths. The death rate is admittedly still relatively low, but it is increasing annually by about 14%. The number of men in whom a prostate tumour has been diagnosed has risen in recent years by 30%, which however should be attributed less to an increasing number of new diseases, but rather to the fact that the population is generally ageing, that methods of diagnosis have improved and that systematic screening programmes were introduced (E. J. Small, D. M. Reese, Curr. Opi. Oncol. 2000, 12, 265-272).

In the early stages prostate tumour growth is androgen-dependent. Provided the tumour is limited locally to the prostate, it can be removed surgically or treated by radiotherapy, but these methods are associated with corresponding risks. In cases in which the tumour is no longer locally limited and has already formed metastases, the tumour is treated by decreasing the supply of androgen to the tumour. This is done either surgically by castration or medically by treatment with antiandrogens (bicalutamide, cyproterone acetate, flutamide), LHRH agonists (leuprolide, goserelin, buserelin, Zoladex), LHRH antagonists (cetrorelix) or 5α-reductase inhibitors (finasteride). Since surgical castration has no effect on adrenal androgen synthesis, more recently combined surgical and drug treatment has often been used (S. Leewansangtong, E. D. Crawford, Endocrine-Related Cancer 1998, 5, 325-339). However, the success of this treatment is only temporary, because as a rule there is regrowth of the tumour after two years at the latest, and in most cases it is then resistant to existing chemical castration therapies (L. J. Denis, K. Griffith, Semin. in Surg. Onc. 2000, 18, 52-74).

There are various indications that in the development and growth of a prostate tumour, the androgen receptor plays an important role not only in the early hormone-dependent, but also in late castration-resistant stages of tumour progression.

The androgen receptor belongs to the family of steroid hormone receptors, which act as ligand-dependent transcription factors. The cytoplasmic androgen receptor, not bound to ligands, forms a complex with chaperones. After binding of androgens to the androgen receptor, there is a change in its conformation. The chaperones dissociate from the complex and the ligand-bound androgen receptor is transported into the cell nucleus. There, after binding to so-called androgen-responsive DNA elements and with the participation of certain co-factors, it activates or suppresses certain target genes (D. J. Lamb et al. Vitam. Horm. 2001, 62, 199-230).

Investigations of prostate tumours show that amplification of the androgen receptor gene locus was detected in 30% of advanced tumours. In other cases a number of mutations were found in the androgen receptor gene, which are localized in various domains of the androgen receptor molecule and lead to altered receptor properties. Mutated receptors can either possess higher affinity for androgens, become constitutively active, alter their ligand specificity, so that they are activated by other steroid hormones or even anti-androgens, be activated through interactions with molecules from other growth-promoting signal transduction pathways, which alter interaction with cofactors, or activate other target genes (J. P. Elo, T. Visakorpi, Ann. Med. 2001, 33, 130-41).

Some clinical findings have been reported concerning the relationship between cancer relapse after anti-androgen drug administration and androgen receptor mutations.

Androgen receptor mutations were observed in 5 out of 17 patients who experienced relapsed prostate cancer after an endocrine therapy with a combination of flutamide and castration, all of which were missense mutations of the amino acid at position 877 of the androgen receptor (Taplin et al., Cancer Res., 59: 2511-2515, 1999). For these mutants at position 877 some anti-androgen drugs, including flutamide, were found to behave as agonists and to stimulate prostate cancer cell proliferation (Veldscholte et al., Biochem. Biophys. Res. Commun., 173: 534-540, 1990).

Haapala et al. (Lab. Invest., 81: 1647-1651, 2001) described different mutations of the androgen receptor, which were identified in biopsy samples from patients who experienced relapsed prostate cancer after an endocrine therapy with a combination of bicalutamide and surgical castration. Three of the detected mutations were missense mutations (G166S, W741C, M749I) and two were silent polymorphisms. None of the investigated tumors showed an amplification of the androgen receptor.

Haapala et al. conclude that different types of androgen receptor alterations in prostate tumors are selected for during various types of hormonal therapy.

Hara et al. (Cancer Research, 63: 149-153, 2003) demonstrated that bicalutamide, which is the most commonly used anti-androgen, acted as an agonist for both the W741C and W741L androgen receptor mutants. The W741C and W741L mutations affect the same codon 741 in the ligand-binding domain of the androgen receptor. In one case codon 741, TGG (tryptophan), is mutated to TGT (cysteine). In the other case it is mutated to TTG (leucine). Within only 6-13 weeks of in vitro exposure to bicalutamide, LNCaP-FGC cells, whose growth had initially been suppressed, came to use bicalutamide as an androgen receptor agonist to survive, due to mutation of the codon 741. Additional evidence that the W741C mutation causes bicalutamide to act as an agonist was provided through data from a xenograft model (Yoshida et al., Cancer Research, 65: 9611-9616, 2005).

Georget et al. (Molecular Endocrinology, 20(4): 724-734, 2006) demonstrate that the E709Y mutation causes the conversion of bicalutamide into a partial agonist.

Investigations with non-steroidal antiandrogens have shown that they have advantages over the steroidal compounds and are therefore to be preferred. Thus, with non-steroidal compounds, a more selective action can be achieved, with fewer side-effects. In contrast to the steroidal antiandrogens, the known non-steroidal drugs bicalutamide and flutamide lack e.g. progestagenic activity and in addition use of them leads to an increase in the serum testosterone level, which clinically might lead to retention of potency (P. Reid, P. Kantoff, W. Oh, Investigational New Drugs 1999, 17, 271-284). Especially against these advanced stages of prostate cancer, despite intensive research in the last 50 years there is still no effective treatment. The 5-year survival rate for these patients is under 15%.

Therefore there is still a great need for new antiandrogens that are suitable for treating and/or preventing hyperproliferative diseases, especially androgen receptor-dependent hyperproliferative diseases, and have advantages over the conventional antiandrogens, such as
- improved activity,
- an improved selectivity profile for treating hyperproliferative diseases,
- an improved profile of side-effects (e.g. fewer undesirable side-effects, reduced toxicity),
- improved physicochemical properties (e.g. solubility in water),
- improved pharmacokinetic properties (e.g. such as leading to a reduction of the necessary dose), or
- a simplified or more economical method of production.

The identification of antiandrogens, which preferably inhibit not only the wild-type form of the androgen receptor (Swiss-Prot Acc. No. P10275, Entry Version 159, Sequence Version 2), but also certain mutated forms of the androgen receptor and/or the cellular growth of cells that overexpress the androgen receptor, would presumably be very useful for treating prostate tumours, even in advanced stages.

There is therefore a need for further compounds that act as androgen receptor antagonists (antiandrogens) and that are suitable for treating prostate cancer, especially of (castration-resistant) prostate cancer.

To date, no N-[4-(quinolin-4-yloxy)cyclohexyl](hetero)arylcarboxamides or N-[4-(quinolin-4-yloxy)cyclohexylmethyl](hetero)arylcarboxamides have been described in the prior art.

The compounds most closely related structurally differ significantly from the structures according to the invention, in that either instead of the cyclohexyl ring they have another ring system (such as an aromatic or heteroaromatic), and/or in that instead of the aromatic group located on the carbonyl group of the amide, they possess a non-aromatic ring bearing an oxo group on one of its ring atoms and/or in that the quinoline is partially hydrogenated and also bears an oxo group. These compounds are, in contrast to the compounds according to the invention, inhibitors of kinases, cytokine MIF or of GPCRs such as the 5-HT2c receptor.

Thus, WO 2006/116713 A1 describes substituted amide derivatives as protein kinase inhibitors for the prevention and treatment of HGF-mediated diseases including cancer and WO 2009/140549 A1 describes combinations of VEGFR inhibitors and hepatocyte growth factor (c-Met) inhibitors for treating cancer, which have, on the carbonyl group of the amide, instead of a (hetero)aromatic ring, a further substituted 3-oxo-2,3-dihydro-1H-pyrazole ring and moreover are substituted with a methoxy group on the quinoline in position 7.

WO 2006/117552 A1 and WO 2005/117570 A1 describe quinolines and quinoxazolines as kinase inhibitors, which possess an aromatic ring instead of the cyclohexyl ring and moreover display on the quinoline ring a substitution pattern that is entirely different from the compounds according to the invention, especially through the complex substituent on position 7, for example a 4-amino-4-cyclopentyloxycarbonylbut-1-yloxy group.

Although the general formula in claim 11 of WO 2010/039248 A1 only allows unsaturated rings between the quinoline and the amide bond, 3 compounds with cyclohexyl ring are described, all of which, however, have another substituted 3-oxo-2,3-dihydro-1H-pyrazole ring instead of the obligatory (hetero)aromatic on the carbonyl group of the amide in the compounds according to the invention. The application relates to methods of cancer treatment, especially with at least one HGF-Met inhibitor and at least one EGFR inhibitor.

In WO 2007/146824 A2, quinolines are proposed as inhibitors of tyrosine kinases for treating hyperproliferative diseases. Out of the total of approx. 100 examples, all of which possess a (hetero)aromatic instead of the cyclohexyl ring, very few are of open-chain amide structure, in which, however, the ring present on the carbonyl group is not a monocyclic aromatic or an aromatic and in the latter case bears an oxo group.

WO 2012/009649 A1 describes MIF inhibitors for treating MIF-associated diseases, which differ structurally even more from the compounds according to the invention, as the quinoline is partially hydrogenated and bears a 2-oxo group and a 3-cyano group, the cyclohexyl ring is replaced with heterocycles such as azetidine, piperidine or pyrrolidine and the oxygen bridge between quinoline and the next ring is absent or occurs as a nitrogen bridge.

It was found, surprisingly, that N-[4-(quinolin-4-yloxy)cyclohexyl](hetero)arylcarboxamides or N-[4-(quinolin-4-yloxy)cyclohexylmethyl](hetero)arylcarboxamides of general formula (I) possess an androgen receptor antagonistic action.

The problem to be solved by the present invention is to provide compounds with androgen receptor antagonistic action for treating hyperproliferative diseases.

This problem is solved according to the invention with the N-[4-(quinolin-4-yloxy)cyclohexyl(methyl)](hetero)arylcarboxamides of general formula (I).

The present invention therefore relates to compounds of general formula (I)

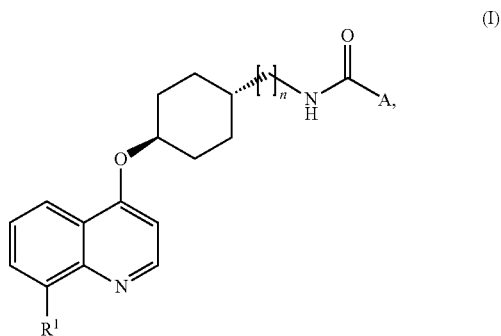

in which

R$^1$ stands for H, cyano, fluorine, chlorine or bromine;

A stands for phenyl or 5-membered heteroaryl, wherein this phenyl or this 5-membered heteroaryl is optionally substituted with one, two or three substituents selected independently of one another from:
halogen, cyano, C$_1$-C$_3$-alkyl-, haloalkyl-, cycloalkyl-, heterocyclyl-, hydroxy, alkoxy-, fluoroalkoxy-, cycloalkyloxy-, amino-, alkylamino-, dialkylamino-, cycloalkylamino-, alkylcycloalkylamino-, dicycloalkylamino-, alkylcarbonylamino-, cycloalkylcarbonylamino-, alkylsulphanyl-, cycloalkylsulphanyl-, alkylsulphonyl-, cycloalkylsulphonyl-, aminosulphonyl-, alkylaminosulphonyl-, cycloalkylaminosulphonyl-; alkoxycarbonyl-;

n=0, 1 or 2;

or one of their salts, of their solvates or of the solvates of their salts.

Compounds according to the invention are the compounds of formula (I) and their salts, solvates and solvates of the salts, the compounds of the formulae stated below covered by formula (I) and their salts, solvates and solvates of the salts and the compounds stated below as practical examples covered by formula (I), and their salts, solvates and solvates of the salts, provided the compounds stated below, covered by formula (I), are not already salts, solvates and solvates of the salts.

In the context of the present invention, physiologically harmless salts of the compounds according to the invention are preferred as "salts". However, salts are also comprised that are not themselves suitable for pharmaceutical uses, but can be used for example for isolating or purifying the compounds according to the invention.

Physiologically harmless salts of the compounds according to the invention comprise acid addition salts of mineral acids, carboxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalene disulphonic acid, acetic acid, trifluoroacetic acid, propionic acid, lactic acid, tartaric acid, malic acid, citric acid, fumaric acid, maleic acid and benzoic acid.

Physiologically harmless salts of the compounds according to the invention also comprise salts of usual bases, such as for example and preferably alkali metal salts (e.g. sodium and potassium salts), alkaline-earth salts (e.g. calcium and magnesium salts) and ammonium salts, derived from ammonia or organic amines with 1 to 16 carbon atoms, for example and preferably ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

"Solvates" means, in the context of the invention, those forms of the compounds according to the invention which, in the solid or the liquid state, form a complex by coordination with solvent molecules. Hydrates are a special form of solvates, in which the coordination takes place with water.

The compounds according to the invention can exist in different stereoisomeric forms depending on their structure, i.e. in the form of configurational isomers or optionally also as conformational isomers (enantiomers and/or diastereomers, including those in the case of atropisomers). The present invention therefore comprises the enantiomers and diastereomers and respective mixtures thereof. The stereoisomerically homogeneous constituents can be isolated in a known manner from said mixtures of enantiomers and/or diastereomers; chromatographic methods are preferably used for this, especially achiral or chiral phase HPLC chromatography.

If the compounds according to the invention can occur in tautomeric forms, the present invention comprises all tautomeric forms.

The present invention also comprises all suitable isotopic variants of the compounds according to the invention. An isotopic variant of a compound according to the invention is in this case to be understood as a compound in which at least one atom within the compound according to the invention is exchanged for another atom of the same atomic number, but with atomic mass different from the atomic mass usually or mainly occurring naturally. Examples of isotopes that can be incorporated in a compound according to the invention are those of hydrogen, carbon, nitrogen, oxygen, sulphur, fluorine, chlorine, bromine and iodine, such as $^2$H (deuterium), $^3$H (tritium), $^{11}$C, $^{13}$C, $^{14}$C, $^{13}$N, $^{15}$N, $^{15}$O, $^{17}$O, $^{18}$O, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I. Particular isotopic variants of a compound according to the invention, such as in particular those in which one or more radioactive isotopes are incorporated, can be of use for example for investigating the mechanism of action or the distribution of active substance in the body; because they can be produced and detected comparatively easily, compounds labelled with $^3$H- or $^{14}$C-isotopes are suitable for this in particular. Furthermore, the incorporation of isotopes, for example deuterium, can lead to certain therapeutic advantages as a result of greater metabolic stability of the compound, such as for example a lengthening of the half-life in the body or a reduction of the effective dose required; said modifications of the compounds according to the invention can therefore optionally also represent a preferred embodiment of the present invention. Isotopic variants of the compounds according to the invention can be produced by methods known by a person skilled in the art, thus for example by the methods described below and the specifications given in the practical examples, using corresponding isotopic modifications of the respective reagents and/or starting compounds.

In addition, the present invention also comprises prodrugs of the compounds according to the invention. The term "prodrugs" comprises compounds which themselves may be biologically active or inactive, but during their residence time in the body are converted to compounds according to the invention (for example metabolically or hydrolytically).

The present invention further relates to all possible crystalline and polymorphic forms of the compounds according to the invention, wherein the polymorphs can be present either as individual polymorphs or as mixtures of several polymorphs in all concentration ranges.

In the context of the present invention, the substituents, unless stated otherwise, have the following meaning:

"Halogen" stands for fluorine, chlorine, bromine and iodine, preferably for fluorine, chlorine and bromine, especially preferably for fluorine and chlorine.

The term "5-membered heteroaryl" stands for an aromatic, monocyclic residue with 5 ring atoms and up to 3, preferably up to 2 heteroatoms from the series S, O and N, for example for oxazolyl, isoxazolyl, pyrazolyl, thienyl, furyl, pyrrolyl, thiazolyl, imidazolyl, preferably for isoxazolyl and pyrazolyl, especially preferably for isoxazolyl.

"Alk" and "alkyl" in alkoxy-, alkylamino-, alkylcycloalkylamino-, alkylcarbonylamino-, alkylsulphanyl-, alkylsulphonyl-, alkylaminosulphonyl-, alkoxycarbonyl- stand for a linear or branched alkyl residue with as a rule 1, 2, 3, 4, 5 or 6, preferably 1, 2 or 3, especially preferably 1 or 2 carbon atoms, for example for methyl, ethyl, propyl, isopropyl, tert-butyl, pentyl and hexyl.

The term "alkyl" stands for a linear or branched alkyl residue with the specifically stated number of carbon atoms. For example the term $C_1$-$C_3$ comprises one, two or three carbon atoms, e.g. methyl, ethyl, propyl, isopropyl. If the number of carbon atoms is not stated specifically, the term "alkyl" stands for a linear or branched alkyl residue with 1, 2, 3, 4, 5 or 6 (=$C_1$-$C_6$-alkyl-) carbon atoms. Alkyl groups with 1, 2 or 3 carbon atoms (=$C_1$-$C_3$-alkyl) are preferred, and methyl is especially preferred.

"Haloalkyl-" stands for partially or fully halogenated alkyl-. In the case of multiply halogenated haloalkyl-, the halogen atoms can be identical or different. Preferred halogen atoms are fluorine or chlorine, especially fluorine. The preferred haloalkyl is trifluoromethyl-.

"Cycloalkyl" stands for a cycloalkyl group with as a rule 3, 4, 5, 6, 7 or 8 (=$C_3$-$C_8$-cycloalkyl), especially 3, 4, 5 or 6 (=$C_3$-$C_6$-cycloalkyl) carbon atoms, for example for cyclopropyl, cyclobutyl, cyclopentyl or cyclohexyl. "Cycloalkyl" preferably stands for $C_3$-$C_6$-cycloalkyl. The term "$C_3$-$C_6$-cycloalkyl" stands for a cycloalkyl group with 3, 4, 5 or 6 carbon atoms.

The term "heterocyclyl" stands for a mono- or polycyclic, preferably mono- or bicyclic, non-aromatic heterocyclic residue with as a rule 4, 5, 6, 7, 8, 9 or 10, preferably 4, 5, 6, 7 or 8 ring atoms and up to 3, preferably up to 2 heteroatoms and/or hetero groups from the series N, O, S, SO, $SO_2$, preferably hetero groups from the series N, O, S. The heterocyclyl residues can be saturated or partially unsaturated, they are preferably saturated. For example we may mention: azetidinyl, oxetanyl, tetrahydrofuranyl, pyrrolidinyl, piperidinyl, morpholinyl, thiomorpholinyl, perhydroazepinyl.

"Alkoxy-" stands for example for methoxy, ethoxy, propoxy, isopropoxy, butoxy, isobutoxy, sec-butoxy, tert-butoxy. "$C_1$-$C_3$-alkoxy-" is preferred, methoxy- is especially preferred.

The term "$C_1$-$C_3$-alkoxy" stands for methoxy-, ethoxy- or propoxy-.

The term "fluoroalkoxy-" refers to an alkoxy residue as defined above, in which one or more hydrogen atoms have been exchanged for one or more fluorine atoms, and "$C_1$-$C_3$-fluoroalkoxy-" is preferred. The term "$C_1$-$C_3$-fluoroalkoxy-" stands for a branched or linear fluoroalkoxy residue with 1, 2 or 3 carbon atoms. For example the term "$C_1$-$C_3$-fluoroalkoxy" stands for trifluoromethoxy-, difluoromethoxy-, tetrafluoroethoxy-, pentafluoroethoxy-, preferably for trifluoromethoxy-.

The term "cycloalkyloxy-" refers to a cycloalkyl residue as defined above, in which a hydrogen atom has been exchanged for an oxygen atom. For example the term stands for cyclopropyloxy-, cyclobutyloxy-, cyclopentyloxy-, cyclohexyloxy- and cycloheptyloxy-, and $C_3$-$C_6$-cycloalkyloxy- is preferred. The term "$C_3$-$C_6$-cycloalkyloxy-" stands for a cycloalkyloxy residue with 3, 4, 5 or 6 carbon atoms, and cyclopropyloxy- is preferred.

"Alkylamino-" stands for an alkylamino residue with a linear or branched alkyl substituent, preferably for $C_1$-$C_3$-alkylamino-. The term "$C_1$-$C_3$-alkylamino-" stands for example for a monoalkylamino residue with 1, 2 or 3 carbon atoms. For example we may mention: methylamino-, ethylamino-, propylamino-, isopropylamino-.

The term "dialkylamino-" stands for an alkylamino residue with two (selected independently of one another) linear or branched alkyl substituents, preferably for ($C_1$-$C_3$)-dialkylamino-. The term "($C_1$-$C_3$)-dialkylamino-" stands for example for a dialkylamino residue with in each case 1, 2 or 3 carbon atoms per alkyl substituent. For example we may mention: dimethylamino-, diethylamino-, ethylmethylamino-, methylpropylamino-, isopropylpropylamino-.

"Cycloalkylamino-" stands for a cycloalkylamino residue with a cycloalkyl substituent, as defined above, preferably for $C_3$-$C_6$-cycloalkylamino-. The term "$C_3$-$C_6$-cycloalkylamino-" stands for example for a monocycloalkylamino residue with 3, 4, 5 or 6 carbon atoms. For example we may mention: cyclopropylamino-, cyclobutylamino-, cyclopentylamino- and cyclohexylamino-, and cyclopropylamino- is preferred.

The term "alkylcycloalkylamino-" stands for an amino residue with two substituents selected independently of one another, an alkyl- and a cycloalkyl substituent, preferably for $C_1$-$C_3$-alkyl-$C_3$-$C_6$-cycloalkylamino-. The term: "$C_1$-$C_3$-alkyl-$C_3$-$C_6$-cycloalkylamino-" stands for example for an amino residue with an alkyl substituent with 1, 2 or 3 carbon atoms and a cycloalkyl residue with 3, 4, 5 or 6 carbon atoms. For example the term "alkylcycloalkylamino-" stands for: butylcyclohexylamino-, propylcyclohexylamino-, ethylcyclohexylamino-, propylcyclopropylamino-, ethylcyclopropylamino-, methylcyclopropylamino-.

The term "dicycloalkylamino-" stands for a cycloalkylamino residue with two (selected independently of one another) cycloalkyl substituents, preferably for ($C_3$-$C_6$)-dicycloalkylamino-. The term "($C_3$-$C_6$)-dicycloalkylamino-" stands for example for a dicycloalkylamino residue with in each case 3, 4, 5 or 6 carbon atoms per cycloalkyl substituent. For example we may mention: dicyclopropylamino-, dicyclohexylamino-, cyclopropylcyclohexylamino-.

The term "alkylcarbonylamino-" stands for a linear or branched alkylcarbonylamino residue with 1, 2, 3, 4, 5 or 6 ("$C_1$-$C_6$-alkylcarbonylamino-"), preferably 1, 2 or 3 carbon atoms ("$C_1$-$C_3$-alkylcarbonylamino-"). Non-limiting examples comprise methylcarbonylamino, ethylcarbonylamino, n-propylcarbonylamino, isopropylcarbonylamino, n-butylcarbonylamino, tert-butylcarbonylamino, n-pentylcarbonylamino and n-hexylcarbonylamino.

The term "cycloalkylcarbonylamino-" stands for a cycloalkylcarbonylamino residue, which for example has 3, 4, 5 or 6 carbon atoms in the cycloalkyl group (=$C_3$-$C_6$-cycloalkylcarbonylamino-). Non-limiting examples comprise cyclopropylcarbonylamino-, cyclobutylcarbonylamino-, cyclopentylcarbonylamino- and cyclohexylcarbonylamino-.

"Alkylsulphanyl-" stands for an alkylsulphanyl residue with a linear or branched alkyl substituent, preferably for $C_1$-$C_3$-alkylsulphanyl-. The term "$C_1$-$C_3$-alkylsulphanyl-" stands for example for an alkylsulphanyl residue with 1, 2 or 3 carbon atoms. For example we may mention: methylsulphanyl-, ethylsulphanyl-, n-propylsulphanyl-, isopropylsulphanyl-.

The term "cycloalkylsulphanyl-" stands for a cycloalkylsulphanyl residue with a cycloalkyl substituent, preferably for $C_3$-$C_6$-cycloalkylsulphanyl. The term "$C_3$-$C_6$-cycloalkylsulphanyl-" stands for example for a cycloalkylsulphanyl residue with 3, 4, 5 or 6 carbon atoms. For example we may mention: cyclopropylsulphanyl-, cyclobutylsulphanyl-, cyclopentylsulphanyl-, cyclohexylsulphanyl-.

"Alkylsulphonyl-" stands for an alkylsulphonyl residue with a linear or branched alkyl substituent, preferably for $C_1$-$C_3$-alkylsulphonyl-. The term "$C_1$-$C_3$-alkylsulphonyl-" stands for example for an alkylsulphonyl residue with 1, 2 or 3 carbon atoms. For example we may mention: methylsulphonyl-, ethylsulphonyl-, n-propylsulphonyl-, isopropylsulphonyl-.

The term "cycloalkylsulphonyl-" stands for a cycloalkylsulphonyl residue with a cycloalkyl substituent, preferably for $C_3$-$C_6$-cycloalkylsulphonyl-. The term "$C_3$-$C_6$-cycloalkylsulphonyl-" stands for example for a cycloalkylsulphonyl residue with 3, 4, 5 or 6 carbon atoms. For example we may mention: cyclopropylsulphonyl-, cyclobutylsulphonyl-, cyclopentylsulphonyl-, cyclohexylsulphonyl-.

"Alkylaminosulphonyl-" stands for an alkylaminosulphonyl residue with one or two (selected independently of one another) linear or branched alkyl substituents, for example for "$C_1$-$C_6$-alkylaminosulphonyl-". The term "$C_1$-$C_6$-alkylaminosulphonyl-" stands for a monoalkylaminosulphonyl residue with 1, 2, 3, 4, 5 or 6 carbon atoms or for a dialkylaminosulphonyl residue with in each case 1, 2, 3, 4, 5 or 6 carbon atoms per alkyl substituent, for example for methylaminosulphonyl-, ethylaminosulphonyl-, n-propylaminosulphonyl-, isopropylaminosulphonyl-, tert-butylaminosulphonyl-, n-pentylaminosulphonyl-, n-hexylaminosulphonyl-, dimethylaminosulphonyl-, diethylaminosulphonyl-, ethylmethylaminosulphonyl-, methyl-n-propylaminosulphonyl-, isopropyl-n-propylaminosulphonyl-, tert-butylmethylaminosulphonyl-, ethyl-n-pentylaminosulphonyl- and n-hexylmethylaminosulphonyl-. "Alkylaminosulphonyl-" preferably stands for "$C_1$-$C_3$-alkylaminosulphonyl-". The term "$C_1$-$C_3$-alkylaminosulphonyl-" stands for example for a monoalkylaminosulphonyl residue with 1, 2 or 3 carbon atoms or for a dialkylaminosulphonyl residue with in each case 1, 2 or 3 carbon atoms per alkyl substituent.

The term "cycloalkylaminosulphonyl-" stands for a cyclolkylaminosulphonyl residue with one or two (selected independently of one another) cycloalkyl substituents, for example for $C_3$-$C_6$-cycloalkylaminosulphonyl- or $C_5$-$C_6$-cycloalkylaminosulphonyl-. We may mention cyclopropylaminosulphonyl-, cyclobutylaminosulphonyl-, cyclopentylaminosulphonyl-, cyclohexylaminosulphonyl-. $C_3$-$C_6$-cycloalkylaminosulphonyl- stands for example for a monocycloalkylaminosulphonyl residue with 3, 4, 5 or 6 carbon atoms or for a dicycloalkylaminosulphonyl residue with in each case 3, 4, 5 or 6 carbon atoms per cycloalkyl substituent.

"Alkoxycarbonyl" stands for a linear or branched alkoxycarbonyl residue with 1 to 6 ($C_1$-$C_6$-alkoxycarbonyl-), preferably 1 to 4 ($C_1$-$C_4$-alkoxycarbonyl-) and especially preferably 1 to 3 carbon atoms ($C_1$-$C_3$-alkoxycarbonyl-). Preferred examples comprise methoxycarbonyl, ethoxycarbonyl, n-propoxycarbonyl, isopropoxycarbonyl and tert-butoxycarbonyl.

In another embodiment, the present invention relates to compounds of formula (I) in which
$R^1$ stands for H, cyano, fluorine or bromine;
A stands for phenyl or 5-membered heteroaryl, wherein this phenyl or this 5-membered heteroaryl is optionally substituted with one or two substituents selected independently of one another from:
halogen, cyano, $C_1$-$C_3$-alkyl-, haloalkyl-;
n=0 or 1;
or one of their salts, of their solvates or of the solvates of their salts.

In another embodiment, the present invention relates to compounds of formula (I) in which
$R^1$ stands for H, cyano, fluorine or bromine;
A stands for phenyl, isoxazolyl or pyrazolyl, wherein this phenyl, isoxazolyl or pyrazolyl is optionally substituted with one or two substituents selected independently of one another from:
fluorine, chlorine, cyano, methyl, trifluoromethyl;
n=0 or 1;
or one of their salts, of their solvates or of the solvates of their salts.

In another embodiment, the present invention relates to compounds of formula (I) in which $R^1$ stands for H, cyano, fluorine, chlorine or bromine.

In another embodiment, the present invention relates to compounds of formula (I) in which $R^1$ stands for H, cyano, fluorine or bromine.

In a preferred embodiment, the present invention relates to compounds of formula (I) in which $R^1$ stands for H or cyano.

In another preferred embodiment, the present invention relates to compounds of formula (I) in which $R^1$ stands for fluorine or cyano.

In another preferred embodiment, the present invention relates to compounds of formula (I) in which $R^1$ stands for fluorine.

In another preferred embodiment, the present invention relates to compounds of formula (I) in which $R^1$ stands for H.

In another preferred embodiment, the present invention relates to compounds of formula (I) in which $R^1$ stands for cyano.

In another embodiment, the present invention relates to compounds of formula (I) in which A stands for phenyl or 5-membered heteroaryl, wherein this phenyl or this 5-membered heteroaryl is optionally substituted with one or two substituents selected independently of one another from:
fluorine, chlorine, cyano, methyl, ethyl, propyl, isopropyl, trifluoromethyl.

In another embodiment, the present invention relates to compounds of formula (I) in which A stands for phenyl, wherein this phenyl is optionally substituted with one or two substituents selected independently of one another from fluorine, chlorine, cyano, methyl, trifluoromethyl.

In another preferred embodiment, the present invention relates to compounds of formula (I) in which A stands for isoxazolyl, wherein this isoxazolyl is optionally substituted with a methyl group.

In an especially preferred embodiment, the present invention relates to compounds of formula (I) in which A stands for methylisoxazolyl, preferably for 5-methylisoxazolyl.

In a preferred embodiment, the present invention relates to compounds of formula (I) in which A stands for phenyl, wherein this phenyl is optionally substituted with a fluoro-substituent.

In an especially preferred embodiment, the present invention relates to compounds of formula (I) in which A stands for fluorophenyl, preferably for 3-fluorophenyl.

In another embodiment, the present invention relates to compounds of formula (I) in which n=0, 1 or 2, preferably n=0 or 1.

The definitions of residues stated in detail in the respective combinations or preferred combinations of residues are also replaced with any other definitions of residues of other combinations independently of the respective combinations of residues stated.

Combinations of two or more of the aforementioned preferred ranges are quite especially preferred.

In another preferred embodiment, the present invention relates to compounds of general formula (I) selected from:
N-({trans-4-[(8-fluoroquinolin-4-yl)oxy]cyclohexyl}methyl)-4-fluorobenzamide,
N-{trans-4-[(8-bromoquinolin-4-yl)oxy]cyclohexyl}-5-methylisoxazole-3-carboxamide,
N-[trans-4-(4-quinolyloxy)cyclohexyl]-3,4-difluorobenzamide,
N-({trans-4-[(8-fluoroquinolin-4-yl)oxy]cyclohexyl}methyl)-3-methylisoxazole-4-carboxamide,
N-({trans-4-[(8-fluoroquinolin-4-yl)oxy]cyclohexyl}methyl)-isoxazole-5-carboxamide,
N-({trans-4-[(8-fluoroquinolin-4-yl)oxy]cyclohexyl}methyl)isoxazole-3-carboxamide,
N-({trans-4-[(8-fluoroquinolin-4-yl)oxy]cyclohexyl}methyl)-5-methylisoxazole-3-carboxamide,
N-({trans-4-[(8-fluoroquinolin-4-yl)oxy]cyclohexyl}methyl)-1H-pyrazole-3-carboxamide,
N-{[trans-4-(4-quinolyloxy)cyclohexyl]methyl}-3,4-difluorobenzamide,
N-{[trans-4-(4-quinolyloxy)cyclohexyl]methyl}-3-fluorobenzamide, N-{[trans-4-(4-quinolyloxy)cyclohexyl]methyl}-5-methyl-isoxazole-3-carboxamide,
N-{trans-4-[(8-bromoquinolin-4-yl)oxy]cyclohexyl}-3-fluorobenzamide,
N-{trans-4-[(8-bromoquinolin-4-yl)oxy]cyclohexyl}-3,4-difluorobenzamide,
N-{trans-4-[(8-bromoquinolin-4-yl)oxy]cyclohexyl}-3-fluoro-4-methylbenzamide,
N-{trans-4-[(8-bromoquinolin-4-yl)oxy]cyclohexyl}-4-cyanobenzamide,
N-{trans-4-[(8-bromoquinolin-4-yl)oxy]cyclohexyl}-3-fluoro-4-(trifluoromethyl)benzamide,
N-{trans-4-[(8-bromoquinolin-4-yl)oxy]cyclohexyl}-4-fluorobenzamide,
N-{trans-4-[(8-cyanoquinolin-4-yl)oxy]cyclohexyl}-3-fluoro-4-methylbenzamide,
4-chloro-N-{trans-4-[(8-cyanoquinolin-4-yl)oxy]cyclohexyl}-3-fluorobenzamide,
N-{trans-4-[(8-cyanoquinolin-4-yl)oxy]cyclohexyl}-3,5-difluorobenzamide,
N-({trans-4-[(8-cyanoquinolin-4-yl)oxy]cyclohexyl}methyl)isoxazole-3-carboxamide,
N-({trans-4-[(8-cyanoquinolin-4-yl)oxy]cyclohexyl}methyl)-5-methylisoxazole-3-carboxamide.

Synthesis of the Compounds According to the Invention:

The production of the compounds according to the invention can be represented by the following synthesis scheme:

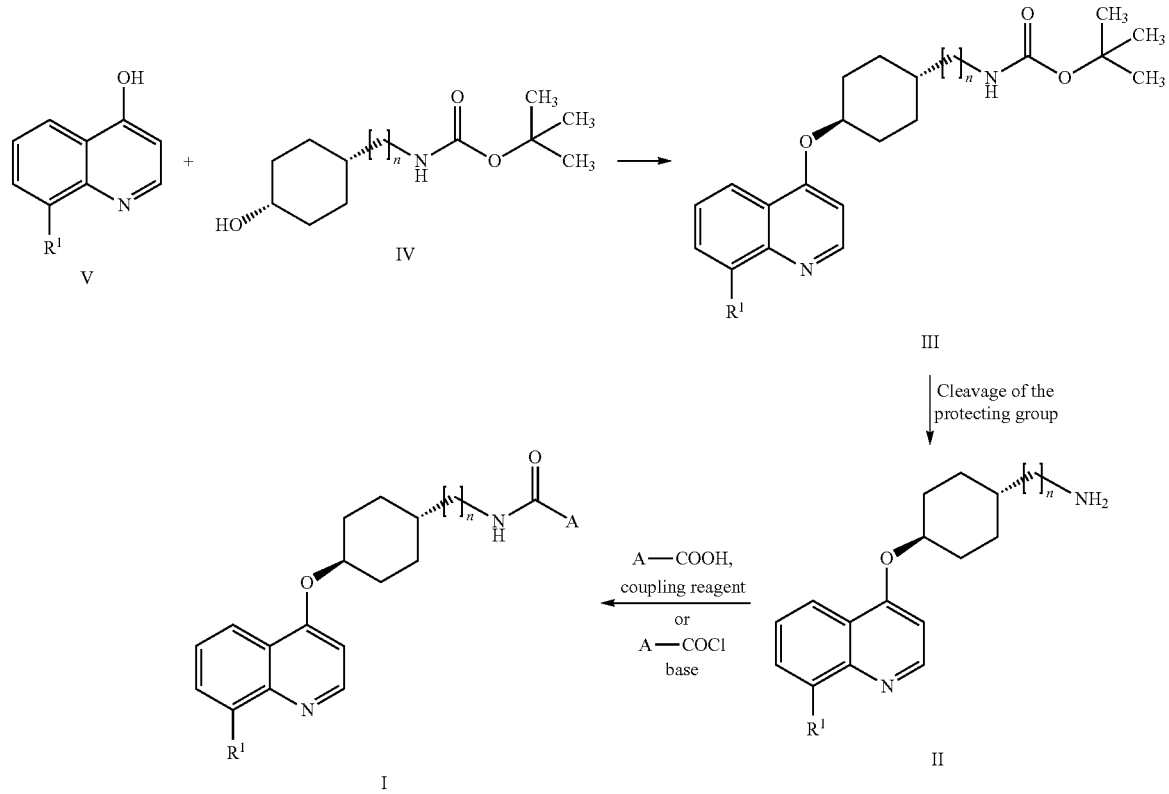

N-{trans-4-[(8-bromoquinolin-4-yl)oxy]cyclohexyl}-3-chloro-4-fluorobenzamide,
N-{trans-4-(4-quinolyloxy)cyclohexyl}-3-fluorobenzamide,
N-({trans-4-[(8-bromoquinolin-4-yl)oxy]cyclohexyl}methyl)-5-methylisoxazole-3-carboxamide,
N-({trans-4-[(8-bromoquinolin-4-yl)oxy]cyclohexyl}methyl)isoxazole-3-carboxamide,
N-{[trans-4-(4-quinolyloxy)cyclohexyl]methyl}-4-cyanobenzamide
N-{trans-4-[(8-cyanoquinolin-4-yl)oxy]cyclohexyl}-3-fluorobenzamide,
N-{trans-4-[(8-cyanoquinolin-4-yl)oxy]cyclohexyl}-3,4-difluorobenzamide,
N-{trans-4-[(8-cyanoquinolin-4-yl)oxy]cyclohexyl}-4-fluorobenzamide,
N-{trans-4-[(8-cyanoquinolin-4-yl)oxy]cyclohexyl}-5-methylisoxazole-3-carboxamide,
3-chloro-N-{trans-4-[(8-cyanoquinolin-4-yl)oxy]cyclohexyl}-4-fluorobenzamide, The invention relates to a method of producing the compounds according to the invention of general formula (I), wherein the compounds according to the invention of general formula (I) are formed by the reaction of the amine building blocks of general formula (II) with an acid chloride A-COCl in the presence of a base or with a carboxylic acid A-COOH in the presence of a suitable coupling reagent and a base. The resulting compounds according to the invention of formula (I) are optionally converted with the corresponding (i) solvents and/or (ii) bases or acids to their solvates, salts and/or solvates of the salts, wherein $R^1$, A and n have the meaning described in connection with the compounds according to the invention of general formula (I).

Suitable organic bases for the reaction of an amine of general formula (II) with an acid chloride A-COCl are for example triethylamine (US2003/232854), pyridine (WO2008/40934) or N-ethyl-N,N-diisopropylamine (WO2009/23655). In connection with the method according to the invention, triethylamine is preferably used as organic base for the reaction of an amine of general formula (II) with a carboxylic acid chloride A-COCl.

The reaction of the amine of general formula (II) with a carboxylic acid chloride A-COCl in the presence of an organic base takes place in aprotic polar solvents such as for example acetonitrile (WO2008/64432), N,N-dimethylformamide (WO2006/117570) or aprotic nonpolar solvents such as for example dichloromethane (US2003/232854). In connection with the method according to the invention, N,N-dimethylformamide (DMF) and pyridine are preferably used as solvents for the reaction of an amine of general formula (II) with a carboxylic acid chloride of general formula A-COCl.

Suitable coupling reagents for the reaction of an amine of general formula (II) with a carboxylic acid A-COOH are for example O-(7-aza-1H-benzotriazol-1-yl)-N,N,N',N'-tetramethyluronium hexafluorophosphate, also called HATU (WO 2005/115972, WO 2006/52722), dicyclohexylcarbodiimide (*J. Am. Chem. Soc.* 1992, 114, 9327 ff.) or a combination of 1H-benzotriazol-1-ol and 1-ethyl-3-[3-(dimethylamino)propyl]carbodiimide hydrochloride (US2007/185148). In connection with the method according to the invention, HATU is preferably used as coupling reagent.

Suitable organic bases for the reaction of an amine of general formula (II) with a carboxylic acid A-COOH are for example 4-(dimethylamino)pyridine (*J. Am. Chem. Soc.* 1992, 114, 9327 ff.), diisopropylethylamine (WO 2005/115972, WO 2006/527522) or triethylamine (US 2007/185148). In connection with the method according to the invention, diisopropylethylamine is preferably used as organic base for the reaction of an amine of general formula (II) with a carboxylic acid A-COOH.

Suitable solvents for this reaction are for example aprotic polar (e.g. N,N-dimethylformamide, see e.g. WO 2005/115972, WO 2006/527522) or aprotic nonpolar solvents (e.g. dichloromethane [US 2007/185148] or tetrahydrofuran [*J. Am. Chem. Soc.* 1992, 114, 9327 ff.]. In connection with the method according to the invention, tetrahydrofuran (THF) and N,N-dimethylformamide (DMF) are preferably used for the reaction of an amine of general formula (II) with a carboxylic acid A-COOH.

The reaction of the amine building blocks of general formula (II) with a carboxylic acid A-COOH or an acid chloride A-COCl takes place at temperatures between 15° C. and 30° C., preferably at room temperature (20° C.). Cooling of the reaction mixture is optionally necessary on adding the reactants in the reaction of the compounds of general formula (II) with an acid chloride A-COCl.

The reaction of the amine building blocks of general formula (II) with an acid chloride A-COCl or a carboxylic acid A-COOH takes place over a period of between 9 and 72 hours, preferably between 12 and 30 hours.

However, for coupling the amide bond, other methods are also suitable, such as condensation between amine and acid using propanephosphonic acid anhydride (T3P) as coupling reagent according to the information in *Org. Lett.* 2011, 5048-5051.

With this procedure, the product is often obtained in solid form after aqueous precipitation, so that recrystallization is required for further purification.

Amine building blocks of general formula (II) result from cleavage of the tert-butylcarbamate protecting group, also known as the Boc protecting group, of the building blocks of general formula (III). For cleavage of the Boc protecting group, a person skilled in the art knows the following methods for example:

using trifluoroacetic acid with dichloromethane as solvent (US 2006/293341)

using a mixture of hydrogen chloride and acetic acid (WO2005/30732)

using a solution of hydrogen chloride in 1,4-dioxane with dichloromethane (WO2008/40934) or acetone (WO2007/91694) as solvent and in a solvent mixture of ethanol and chloroform (WO2004/67516).

Trifluoroacetic acid is preferably used for cleavage of the tert-butylcarbamate group.

The present invention also relates to amine building blocks of general formula (II)

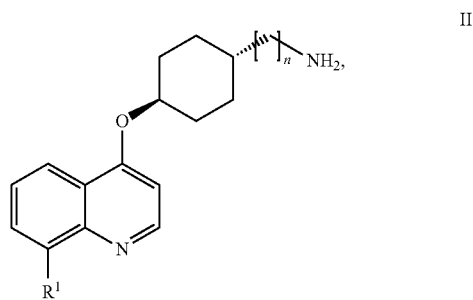

in which $R^1$ and n have the meaning described in connection with the compounds according to the invention of general formula (I).

N-Boc protected amino(methyl)cyclohexanol building blocks of general formula (IV) are commercially available both as cis/trans mixture and as pure trans-isomer (ABCR, Betapharm). The following method was used for preparing the building blocks of general formula (III), starting from cis-isomers of the alcohol building blocks of general formula (IV) and commercially available 4-hydroxyquinoline derivatives (Aldrich, Activate) of general formula (V):

using diisopropylazodicarboxylate, also called DIAD, with triphenylphosphine in tetrahydrofuran (EP1712235) or in toluene as alternative solvent (EP1550657) at room temperature. Instead of diisopropylazodicarboxylate, it is also possible to use diethylazodicarboxylate (DEAD).

Using this method, the stereochemistry on the carbinol centre of the building blocks of general formula (IV) is inverted in the reaction (Mitsunobu, O. *Synthesis*, 1981, 1-28)

The cis building blocks of general formula (IV) can be prepared by inversion of the carbinol centre by means of the so-called Mitsunobu reaction (Mitsunobu, O. *Synthesis*, 1981, 1-28).

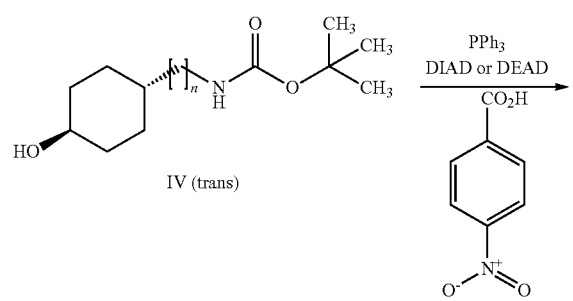

-continued

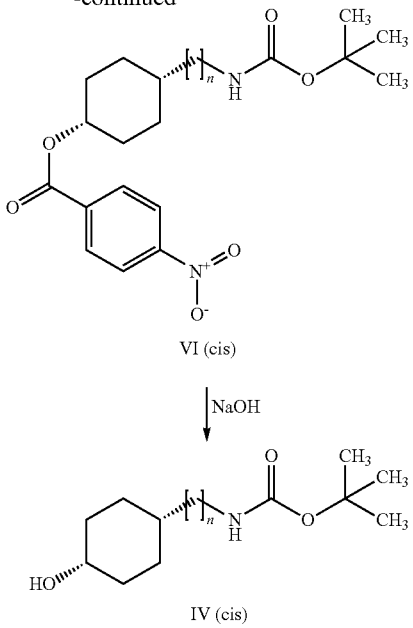

Alternatively, the cis-building block aminocyclohexanol (n=0) can also be prepared in the following way described in the literature: *Tet. Lett.* 1998, 39. 2059-2062.

The following alternative synthesis route can be used for preparing the compounds according to the invention of general formula (I) that have a cyano substituent on the quinoline C8 (compounds of general formula (VIII)). Starting from derivatives bromine-substituted on the quinoline C8 of general formula (VII), the cyano group can be inserted by means of a bromine/cyano exchange reaction (*J. Org. Chem.* 2005, 70, 1508-1510).

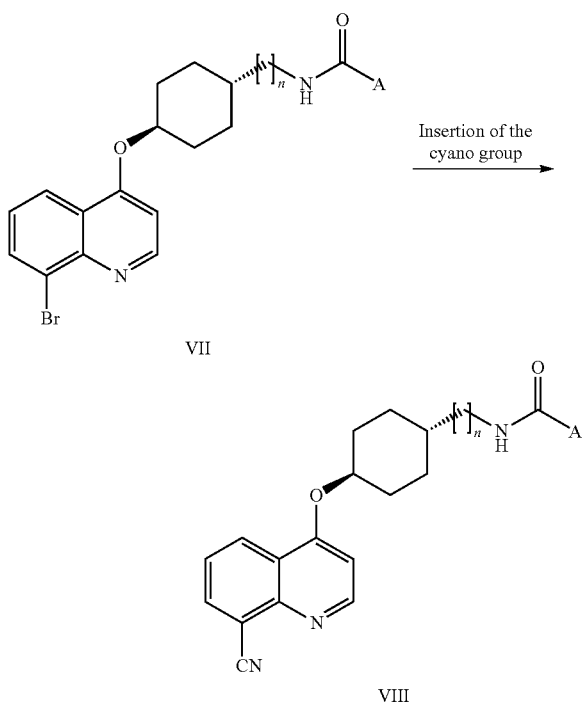

The compounds according to the invention display an unforeseeable, valuable pharmacological and pharmacokinetic spectrum of action. They are therefore suitable for use as medicinal products for treating and/or preventing diseases in humans and animals.

The term "treatment" in the context of the present invention includes prophylaxis.

The pharmaceutical efficacy of the compounds according to the invention can be explained by their action as antagonists of the androgen receptor.

The present invention further relates to the use of the compounds according to the invention for treating and/or preventing diseases, preferably hyperproliferative diseases, especially preferably androgen receptor-dependent hyperproliferative diseases.

The hyperproliferative diseases that can be treated using the compounds according to the invention include in particular the group of cancer and tumour diseases. In the context of the present invention, these include in particular the following diseases, but are not limited to these: breast carcinomas and breast tumours (breast cancers including ductal and lobular forms, also in situ), respiratory tract tumours (small-cell and non-small-cell carcinoma, bronchial carcinomas), brain tumours (e.g. of the brain stem and hypothalamus, astrocytoma, ependymoma, glioblastoma, gliomas, medulloblastoma, meningiomas and neuroectodermal and pineal tumours), tumours of the digestive organs (oesophageal, gastric, gallbladder, small intestine, colon, rectum and anal carcinomas), liver tumours (including hepatocellular carcinoma, cholangiocarcinoma and mixed hepatocellular cholangiocarcinoma), tumours of the head and neck (larynx, hypopharynx, nasopharynx, oropharynx, lip and oral cavity carcinomas, oral melanomas), skin tumours (basaliomas, prickle-cell carcinomas, squamous cell carcinomas, Kaposi sarcoma, malignant melanomas, non-melanoma-like skin cancer, Merkel cell skin cancer, mast cell tumours), tumours of the supporting and connective tissue (including soft tissue sarcomas, osteosarcomas, malignant fibrous histiocytomas, chondrosarcomas, fibrosarcomas, hemangiosarcomas, leiomyosarcomas, liposarcomas, lymphosarcomas and rhabdomyosarcomas), tumours of the eye (including intraocular melanoma and retinoblastoma), tumours of the endocrine and exocrine glands (e.g. of the thyroid and parathyroid, pancreas and salivary gland carcinomas, adenocarcinomas), tumours of the urinary tract (bladder, penis, kidney, renal pelvis and ureter tumours) and tumours of the reproductive organs (endometrial, cervical, ovarian, vaginal, vulval and uterine carcinomas in women and prostate and testicular carcinomas in men). They also include proliferative diseases of the blood, of the lymphatic system and spinal cord, in solid form and as circulating cells, such as leukaemias, lymphomas and myeloproliferative diseases, e.g. acute myeloid, acute lymphoblastic, chronic-lymphocytic, chronic-myelogenic and hairy cell leukaemia, and AIDS-related lymphomas, Hodgkin lymphomas, non-Hodgkin lymphomas, cutaneous T cell lymphomas, Burkitt lymphomas and lymphomas in the central nervous system.

These well-characterized human diseases can also occur with comparable aetiology in other mammals, where they can also be treated with the compounds of the present invention.

The treatment of the aforementioned cancer diseases using the compounds according to the invention comprises both treatment of solid tumours and treatment of metastasized or circulating forms thereof.

The term "treatment" or "treat" is used conventionally in the context of this invention and means the care and management of a patient with the aim of combating, reducing, attenuating or alleviating a disease or disorder and improving the quality of life, which is impaired by said disease, such as for example a cancer disease.

Preferably, the compounds according to the invention are suitable for treating and/or preventing androgen receptor-dependent hyperproliferative diseases.

The term "androgen receptor-dependent hyperproliferative disease", in connection with the present invention, means in particular androgen-dependent prostate cancer, castration-resistant prostate cancer, benign hyperplasia of the prostate (BHP) and benign hyperproliferative diseases of the endometrium (e.g. endometriosis) and of the myometrium (e.g. uterine fibroids, uterine leiomyomata).

Preferably, the compounds according to the invention can be used for treating and/or preventing hyperproliferative diseases of the myometrium, especially for treating and/or preventing uterine fibroids and/or uterine leiomyomata. WO2011029782 shows that antagonists of the androgen receptor are suitable in principle for treating and/or preventing hyperproliferative diseases of the myometrium.

Preferably, the compounds according to the invention can be used for treating and/or preventing prostate cancer, especially preferably androgen-dependent prostate cancer, castration-resistant prostate cancer and benign hyperplasia of the prostate (BHP).

Especially preferably, the compounds according to the invention can be used for treating and/or preventing castration-resistant prostate cancer.

The present invention further relates to the use of the compounds according to the invention for treating and/or preventing diseases in women that are accompanied by a raised androgen level, especially of PCOS (polycystic ovary syndrome) and hirsutism, preferably for treating and/or preventing PCOS.

In women, various syndromes are described that are caused by an increased rate of synthesis and availability of androgens. The aetiology of the increased androgen synthesis and action is as a rule unknown; a tumour is only found as the trigger in a few cases [D Rachoń, Differential diagnosis of hyperandrogenism in women with polycystic ovary syndrome, Exp Clin Endocrinol Diabetes, 2012, 120(4): 205-209]. The symptoms produced can occur independently of one another, or together, but they all have in common a raised androgen level in the women's blood, which also constitutes an important diagnostic marker [Amsterdam ESHRE/ASRM-sponsored 3rd PCOS Consensus Workshop Group Consensus on women's health aspects of polycystic ovary syndrome (PCOS), Hum Reprod., 2012, 27(1): 14-24]. Polycystic ovary syndrome (PCOS) is characterized by many immature follicles with arrested development in a woman's ovary, which through increased LH-stimulation have increased release of androgens [S. Yarak et al., Hyperandrogenism and skin: polycystic ovary syndrome and peripheral insulin resistance. An. Bras. Dermatol. [online] 2005, 80(4): 395-410]. A raised androgen level in women's blood, which is caused by PCOS, but can also have other causes, is causal for the development of hirsutism, i.e. a male pattern of hair growth with for example visible beard growth, but also growth of hair on the chest or on the back. Furthermore, owing to the raised androgen level, many women display insulin resistance and later develop diabetes [Amsterdam ESHRE/ASRM-Sponsored 3rd PCOS Consensus Workshop Group Consensus on women's health aspects of polycystic ovary syndrome (PCOS), Hum Reprod, 2012, 27(1): 14-24].

The pure antiandrogen flutamide is being used successfully for treating the various symptoms of androgen excess in women. Treatment with flutamide leads to a reduction of the male pattern of hair growth in women with hirsutism [I I Müderris et al., A comparison between two doses of flutamide (250 mg/d and 500 mg/d) in the treatment of hirsutism, Fertil Steril., 1997, 68(4): 644-7]. Current practice for treating PCOS is the combination of an antiandrogen with a drug against diabetes [Amsterdam ESHRE/ASRM-sponsored 3rd PCOS, Consensus Workshop Group Consensus on women's health aspects of polycystic ovary syndrome (PCOS), Hum Reprod, 2012, 27(1): 14-24]. The antiandrogen flutamide can, however, also be used alone for treating PCOS and the diabetes that often accompanies it [A Gambineri et al., Effect of flutamide and metformin administered alone or in combination in dieting obese women with polycystic ovary syndrome, Clin Endocrinol, 2004, 60: 241-249]; obviously the antiandrogen alone also leads to an improved uptake of glucose in cells under stimulation with insulin [A Corbould Chronic testosterone treatment induces selective insulin resistance in subcutaneous adipocytes of women, J Endocrinol, 2007, 192: 585-594]. At present there is no really suitable selective antiandrogen for long-term treatment in women. Flutamide can cause acute liver failure, especially in women [J Brahm et al., Acute and fulminant hepatitis induced by flutamide: case series report and review of the literature, Ann Hepatol, 2011, 10(1): 93-8]. Bicalutamide is hardly used in women of reproductive age. Owing to its long and variable pharmacokinetic half-life of up to 10 days, the antiandrogenic action cannot be cancelled quickly enough for reliably avoiding injury to a male fetus if the woman unexpectedly becomes pregnant [I D Cockshott et al., The pharmacokinetics of Casodex in prostate cancer patients after single and during multiple dosing, Eur Urol, 1990, 18 Suppl 3: 10-17; H M Scott et al., Steroidogenesis in the fetal testis and its susceptibility to disruption by exogenous compounds, Endocr Rev, 2009, 30(7): 883-925]. In order to rule out malformation of a fetus, antiandrogens are therefore often combined with an oral contraceptive. For the combination with a gestagen in an oral contraceptive, the antiandrogen should not affect the degradation of the gestagens. Alternatively, antiandrogenic gestagens are used for treating PCOS and hirsutism; as in this case both effects are produced by one molecule, the antiandrogenic action cannot be dosed optimally.

Therefore for reliable and effective treatment of diseases in women that can be caused by androgen excess, e.g. by PCOS, e.g. hirsutism and diabetes, there is no compatible, selective antiandrogen with a pharmacokinetic half-life of less than three, preferably less than two days, which only interferes with the action of gestagens to a slight extent, and preferably not at all.

The present invention further relates to the use of the compounds according to the invention for treating and/or preventing diseases, especially the aforementioned diseases.

The present invention further relates to the compounds according to the invention for use as medicinal products.

The present invention further relates to the use of the compounds according to the invention for producing a medicinal product for treating and/or preventing diseases, especially the aforementioned diseases.

The present invention further relates to the compounds according to the invention for use for treating and/or preventing diseases, especially the aforementioned diseases.

The present invention further relates to the use of the compounds according to the invention in a method for treating and/or preventing diseases, especially the aforementioned diseases.

The present invention further relates to a method for treating and/or preventing diseases, especially the aforementioned diseases, using an effective amount of at least one of the compounds according to the invention.

The compounds according to the invention can be used alone or if required in combination with one or more other pharmacologically effective substances, provided this combination does not lead to undesirable and unacceptable side-effects.

The present invention therefore further relates to medicinal products containing at least one compound according to the invention and one or more other active substances, especially for treating and/or preventing the aforementioned diseases.

For example, the compounds of the present invention can be combined with known anti-hyperproliferative, cytostatic or cytotoxic substances for treating cancer diseases. Furthermore, the compounds according to the invention can also be used in combination with radiotherapy and/or surgery.

The following may be mentioned as examples of suitable combination active substances: 131I-chTNT, abarelix, abiraterone, aclarubicin, aldesleukin, alemtuzumab, alitretinoin, altretamine, aminoglutethimide, amrubicin, amsacrine, anastrozole, arglabin, arsenic trioxide, asparaginase, azacitidine, basiliximab, BAY 80-6946, BAY 1000394, refametinib (BAY 86-9766, RDEA 119), belotecan, bendamustine, bevacizumab, bexarotene, bicalutamide, bisantrene, bleomycin, bortezomib, buserelin, busulfan, cabazitaxel, calcium folinate, calcium levofolinate, capecitabine, carboplatin, carmofur, carmustine, catumaxomab, celecoxib, celmoleukin, cetuximab, chlorambucil, chlormadinone, chlormethine, cisplatin, cladribine, clodronic acid, clofarabine, crisantaspase, cyclophosphamide, cyproterone, cytarabine, dacarbazine, dactinomycin, darbepoetin alfa, dasatinib, daunorubicin, decitabine, degarelix, denileukin diftitox, denosumab, deslorelin, dibrospidium chloride, docetaxel, doxifluridine, doxorubicin, doxorubicin+estrone, eculizumab, edrecolomab, elliptinium acetate, eltrombopag, endostatin, enocitabine, epirubicin, epitiostanol, epoetin alfa, epoetin beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glutoxim, goserelin, histamine dihydrochloride, histrelin, hydroxycarbamide, I-125 seeds, ibandronic acid, ibritumomab tiuxetan, idarubicin, ifosfamide, imatinib, imiquimod, improsulfan, interferon alfa, interferon beta, interferon gamma, ipilimumab, irinotecan, ixabepilone, lanreotide, lapatinib, lenalidomide, lenograstim, lentinan, letrozole, leuprorelin, levamisole, lisuride, lobaplatin, lomustine, lonidamine, masoprocol, medroxyprogesterone, megestrol, melphalan, mepitiostane, mercaptopurine, methotrexate, methoxsalen, methyl aminolevulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, ofatumumab, omeprazole, oprelvekin, oxaliplatin, p53 gene therapy, paclitaxel, palifermin, palladium-103 seed, pamidronic acid, panitumumab, pazopanib, pegaspargase, PEG-epoetin beta (methoxy PEG-epoetin beta), pegfilgrastim, peginterferon alfa-2b, pemetrexed, pentazocine, pentostatin, peplomycin, perfosfamide, picibanil, pirarubicin, plerixafor, plicamycin, poliglusam, polyestradiol phosphate, polysaccharide-K, porfimer sodium, pralatrexate, prednimustine, procarbazine, quinagolide, radium-223 chloride, raloxifene, raltitrexed, ranimustine, razoxane, regorafenib, risedronic acid, rituximab, romidepsin, romiplostim, sargramostim, sipuleucel-T, sizofiran, sobuzoxane, sodium glycididazole, sorafenib, streptozocin, sunitinib, talaporfin, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, trabectedin, trastuzumab, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbine, vorinostat, vorozole, yttrium-90 glass microspheres, zinostatin, zinostatin stimalamer, zoledronic acid, zorubicin.

The present invention preferably relates to medicinal products containing at least one compound according to the invention and one or more of the following active substances, especially for treating and/or preventing androgen receptor-dependent proliferative diseases:

LHRH (luteinizing hormone-releasing hormone) agonists,
LHRH (luteinizing hormone-releasing hormone) antagonists,
C(17,20)-lyase inhibitors,
5-alpha-reductase inhibitors type I,
5-alpha-reductase inhibitors type II,
mixed 5-alpha-reductase inhibitors type I/II,
radiopharmaceuticals emitting alpha-radiation for treating bone metastases, e.g. radium-223 chloride,
cytostatics,
VEGF (vascular endothelial growth factor)-kinase inhibitors,
anti-gestagens,
anti-oestrogens,
EGF antibodies,
oestrogens, or
other androgen receptor antagonists.

The present invention further relates to the medicinal products according to the invention for use for treating and/or preventing diseases, especially the aforementioned diseases.

The compounds according to the invention can have systemic and/or local action. For this purpose they can be applied in a suitable way, for example by the oral, parenteral, pulmonary, nasal, sublingual, lingual, buccal, rectal, dermal, transdermal, conjunctival, or otic route or as implant or stent.

The compounds according to the invention can be administered in suitable dosage forms for these routes of application.

For oral application, dosage forms are suitable that function according to the prior art with rapid and/or modified release of the compounds according to the invention, and contain the compounds according to the invention in crystalline and/or amorphized and/or dissolved form, for example tablets (uncoated or coated tablets, for example with enteric coatings or coatings with delayed dissolution or insoluble coatings, which control the release of the compound according to the invention), tablets that quickly disintegrate in the oral cavity or films/wafers, films/lyophilizates, capsules (for example hard or soft gelatin capsules), sugar-coated pills, granules, pellets, powders, emulsions, suspensions, aerosols or solutions.

Parenteral application can take place bypassing an absorption step (e.g. intravenous, intraarterial, intracardiac, intraspinal or intralumbar) or with inclusion of absorption (e.g. intramuscular, subcutaneous, intracutaneous, percutaneous or intraperitoneal). Suitable dosage forms for parenteral application include preparations for injection and infusion in the form of solutions, suspensions, emulsions, lyophilizates or sterile powders.

Suitable dosage forms for the other routes of application are for example inhalation dosage forms (including powder inhalers, nebulizers), nasal drops, solutions, and sprays; tablets, films/wafers or capsules for lingual, sublingual or buccal application, suppositories, ear or eye preparations, vaginal capsules, aqueous suspensions (lotions, shaking mixtures), lipophilic suspensions, ointments, creams, transdermal therapeutic systems (for example patches), milks, pastes, foams, dusting powders, implants or stents.

The compounds according to the invention can be transformed into the dosage forms listed above. This can take place in a manner known per se by mixing with inert, non-toxic, pharmaceutically suitable excipients. These excipients include carriers (for example microcrystalline cellulose, lactose, mannitol), solvents (e.g. liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (e.g. antioxidants, for example ascorbic acid), colorants (e.g. inorganic pigments, for example iron oxides) and taste and/or odour correctants.

The present invention further relates to medicinal products that contain at least one compound according to the invention, usually together with one or more inert, non-toxic, pharmaceutically suitable excipients, and the use thereof for the aforementioned purposes.

The following practical examples explain the invention. The invention is not restricted to the examples.

The percentages in the following tests and examples are, unless stated otherwise, percentages by weight; parts are parts by weight. Proportions of solvents, dilution ratios and concentration figures for liquid/liquid solutions always refer to the volume.

EXAMPLES

Abbreviations

DMSO dimethylsulphoxide
HATU O-(7-azabenzotriazol-1-yl)-N,N,N',N'-tetramethyluronium hexafluorophosphate
DIAD diisopropylazodicarboxylate
DEAD diethylazodicarboxylate
HPLC high-pressure (high-performance) liquid chromatography
MHz megahertz
MS mass spectroscopy
m/z mass per charge
NMR nuclear magnetic resonance spectroscopy
ppm parts per million
RT retention time
T3P propanephosphonic acid cycloanhydride

Preparation of the Building Blocks

Building Block A1 cis-4-[(tert-butoxycarbonyl)aminomethyl]cyclohexyl-4-nitrobenzoate

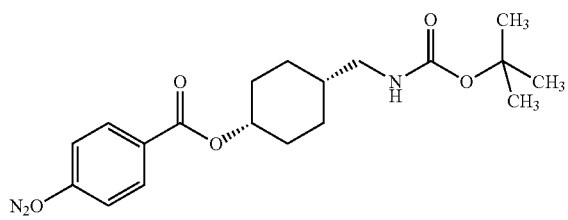

Tert-butyl [(trans-4-hydroxycyclohexyl)methyl]carbamate (5.0 g, 21.15 mmol), 4-nitrobenzoic acid (5.3 g, 31.72 mmol) and triphenylphosphine (8.32 g, 31.72 mmol) were put in tetrahydrofuran (290 mL). After adding diethylazodicarboxylate (13.81 g, 31.72 mmol), the reaction mixture was stirred for 20 hours at room temperature. Water was added, and it was extracted twice with ethyl acetate. The combined organic phases were then washed with saturated aqueous sodium chloride solution and dried over sodium sulphate. After removing the drying agent and solvent residues, followed by chromatography of the residue, the desired product was obtained at 60% yield (4.81 g).

$^1$H NMR (400 MHz, DMSO-$d_6$) δ [ppm] 1.20-1.65 (m, 16H), 1.80-1.90 (m, 2H), 2.75-2.85 (m, 2H), 5.10-5.20 (m, 1H), 6.80-6.90 (m, 1H), 8.15 (d, 2H), 8.35 (d, 2H)

Building Block A2 tert-butyl N-[(cis-4-hydroxycyclohexyl)methyl]carbamate

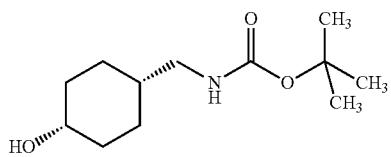 [SMILES: CC(C)(C)OC(=O)NC[C@H]1CC[C@@H](O)CC1]

cis-4-[(tert-Butoxycarbonyl)aminomethyl]cyclohexyl-4-nitrobenzoate (4.81 g, 12.7 mmol) was dissolved in methanol (345 mL) and sodium hydroxide (10.17 g, 254.2 mmol) was added. After 20 hours at room temperature, methanol was removed under vacuum. The residue was taken up in water and extracted with ethyl acetate. After drying the organic phase over sodium sulphate, and removing the drying agent and solvent residues under vacuum, the product was obtained at 88% yield (2.57 g), and was used without purification in the next reaction.

$^1$H NMR (300 MHz, DMSO-$d_6$) δ [ppm] 1.18-1.38 (m, 14H), 1.40-1.60 (m, 2H), 2.74 (t, 2H) 3.66 (m, 1H), 4.19 (d, 1H), 6.74 (t, 1H)

Building Block A3 tert-butyl-N-(cis-4-hydroxycyclohexyl)carbamate

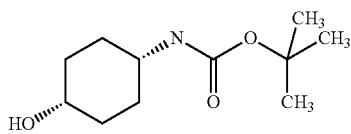

This building block was obtained according to information in the literature: *Tet. Lett.* 1998, 39, 2059-2062.

Building Block B1 tert-butyl-N-({trans-4-[(8-fluoroquinolin-4-yl)oxy]cyclohexyl}methyl)carbamate

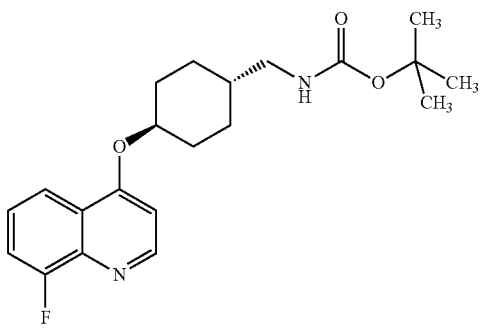 [SMILES: CC(C)(C)OC(=O)NC[C@H]1CC[C@H](Oc2ccnc3c(F)cccc23)CC1]

8-Fluoroquinolin-4-ol (948 mg, 5.81 mmol), triphenylphosphine (1.52 g, 5.81 mmol) and DIAD (1.17 g, 5.81 mmol) were dissolved in tetrahydrofuran (140 mL). After adding tert-butyl-N-[(cis-4-hydroxycyclohexyl)methyl]carbamate (1.11 g, 4.84 mmol), the reaction mixture was stirred overnight at room temperature. The reaction mixture was diluted with water, extracted with ethyl acetate and the combined organic phases were dried over sodium sulphate. After removal of the solvent residues and chromatographic purification of the residue, the product was obtained at 42% yield (960 mg).

$^1$H NMR (300 MHz, DMSO-$d_6$) δ [ppm] 1.05-1.19 (m, 2H), 1.35 (s, 9H), 1.38-1.52 (m, 2H), 1.70-1.82 (m, 2H), 2.08-2.20 (m, 2H), 2.80 (t, 2H), 4.52-4.69 (m, 1H), 6.84 (t, 1H), 7.16 (d, 1H), 7.39-7.61 (m, 2H), 7.83-7.93 (m, 1H), 8.69 (d, 1H)

The following building blocks in Table 1 were prepared similarly.

TABLE 1

| Building block | Structure | Analysis data | Yield |
|---|---|---|---|
| B2 | tert-butyl-N-{[trans-4-(4-quinolyloxy)cyclohexyl]methyl}carbamate | MS ESI+: m/z 357 | 34% |
| B3 | tert-butyl-N-{trans-4-[(8-bromoquinolin-4-yl)oxy]cyclohexyl}-carbamate | $^1$H NMR (300 MHz, DMSO-$d_6$) δ [ppm] 1.36 (s, 11 H), 1.47-1.63 (m, 2 H), 1.78-1.89 (m, 2 H), 2.07-2.19 (m, 2 H), 3.30-3.40 (m, 1 H), 4.57-4.70 (m, 1 H), 6.87 (d, 1 H), 7.20 (d, 1 H), 7.40 (t, 1 H), 8.01-8.16 (m, 2 H), 8.75 (d, 1 H) | 58% |
| B4 | tert-butyl-N-[trans-4-(4-quinolyloxy)cyclohexyl]carbamate | $^1$H NMR (300 MHz, CDCl3) δ [ppm] 1.30-1.55 (m, 11 H), 1.47-1.63 (m, 2 H), 1.64-1.84 (m, 2 H), 2.10-2.35 (m, 4 H), 3.50-3.70 (m, 1 H), 4.35-4.60 (m, 2 H), 6.71 (d, 1 H), 7.48 (t, 1 H), 7.68 (t, 1 H), 8.04 (dd, 1 H), 8.20 (dd, 1 H), 8.70 (d, 1 H) | 48% |

Building Block C1 trans-{4-[(8-fluoroquinolin-4-yl)oxy]cyclohexyl}methylamine

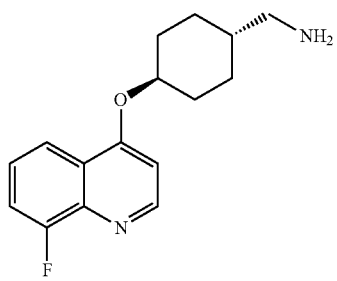 [SMILES: NC[C@H]1CC[C@H](Oc2ccnc3c(F)cccc23)CC1]

tert-Butyl-N-({trans-4-[(8-fluoroquinolin-4-yl)oxy]cyclohexyl}methyl)carbamate (950 mg, 2.54 mmol) was dissolved in dichloromethane (7.0 mL) and trifluoroacetic acid (2.0 mL, 25.4 mmol) was added at room temperature. After one hour at room temperature the reaction mixture was concentrated by evaporation and was then coevaporated with toluene. The residue was taken up in ammoniacal methanol solution (7 N) and concentrated by evaporation again to dryness. After chromatography, the desired product was obtained at 68% yield (470 mg).

$^1$H NMR (400 MHz, DMSO-$d_6$) δ [ppm] 1.02-1.14 (m, 2H), 1.21-1.34 (m, 1H), 1.39-1.51 (m, 2H), 1.80-1.89 (m, 2H), 2.13-2.20 (m, 2H), 3.13 (s, 2H), 4.56-4.66 (m, 1H), 7.15 (d, 1H), 7.48-7.55 (m, 2H), 7.86-7.93 (m, 1H), 8.69 (d, 1H)

The following building blocks in Table 2 were prepared similarly.

TABLE 2

| Building block | Structure | Analysis data | Yield |
|---|---|---|---|
| C2 | trans-[4-(quinolyloxy)cyclohexyl]-methylamine | $^1$H NMR (500 MHz, DMSO-$d_6$) δ [ppm] 1.17-1.29 (m, 2 H), 1.47-1.58 (m, 2 H), 1.62-1.73 (m, 1 H), 1.87-1.96 (m, 2 H), 2.21-2.29 (m, 2 H), 2.72-2.78 (m, 2 H), 4.63-4.71 (m, 1 H), 7.12 (d, 1 H), 7.53-7.58 (m, 1 H), 7.72-7.77 (m, 1 H), 7.94 (d, 1 H), 8.13-8.17 (m, 1 H), 8.72 (d, 1 H) | 27% |
| C3 | trans-4-[(8-bromoquinolin-4-yl)oxy]cyclohexylamine | $^1$H NMR (300 MHz, DMSO-$d_6$) δ [ppm] 1.26 (s, 2 H), 1.42-1.63 (m, 2 H), 1.73-1.89 (m, 2 H), 2.03-2.16 (m, 2 H), 2.60-2.76 (m, 1 H), 4.52-4.72 (m, 1 H), 7.17 (d, 1 H), 7.41 (t, 1 H), 8.00-8.17 (m, 2 H), 8.76 (d, 1 H) | 78% |
| C4 | trans-4-(4-quinolyloxy)cyclohexylamine | The product was used in the next step without further purification. | 79% |

TABLE 2-continued

| Building block | Structure | Analysis data | Yield |
|---|---|---|---|
| C5 | ![structure](trans-{4-[(8-bromoquinolin-4-yl)oxy]cyclohexyl}methylamine) | $^1$H NMR (300 MHz, CDCl$_3$) δ [ppm] 1.08-2.05 (ser m, 11 H), 2.25-2.35 (m, 2 H), 2.62 (d, 2 H), 4.40-4.55 (m, 1 H), 6.80 (d, 1 H), 7.30 (t, 1 H), 8.02 (d, 1 H), 8.20 (d, 1 H), 8.86 (d, 1 H) | 45% |

[trans-{4-[(8-bromoquinolin-4-yl)oxy]cyclohexyl}methylamine]

Example 1
N-({trans-4-[(8-fluoroquinolin-4-yl)oxy]cyclohexyl}methyl)-4-fluorobenzamide

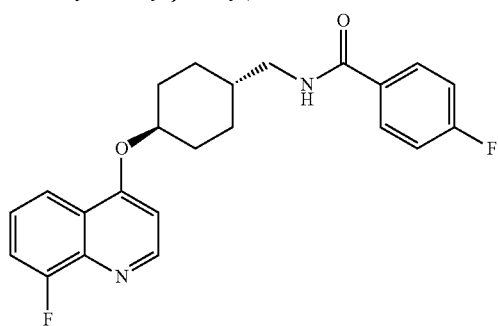

{trans-4-[(8-Fluoroquinolin-4-yl)oxy]cyclohexyl}methylamine (1.82 g mg, 6.63 mmol) was dissolved in tetrahydrofuran (415 mL). After adding HATU (2.78 g, 7.30 mmol), diisopropylethylamine (1.30 mL, 7.30 mmol) and 4-fluorobenzoic acid (1.02 g, 7.30 mmol), the reaction mixture was stirred overnight at room temperature. After chromatography, the desired product was obtained at 71% yield (1.96 g).

$^1$H NMR (400 MHz, DMSO-d$_6$) δ [ppm] 1.19-1.29 (m, 2H), 1.43-1.56 (m, 2H), 1.60-1.70 (m, 1H), 1.80-1.90 (m, 2H), 2.14-2.24 (m, 2H), 3.18 (t, 2H), 4.57-4.76 (m, 1H), 7.19 (d, 1H), 7.28 (t, 2H), 7.42-7.59 (m, 2H), 7.86-7.97 (m, 3H), 8.50 (t, 1H), 8.72 (d, 1H)

Example 2
N-{trans-4-[(8-bromoquinolin-4-yl)oxy]cyclohexyl}-5-methylisoxazole-3-carboxamide

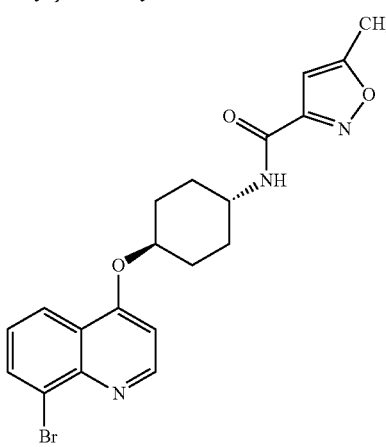

trans-4-[(8-Bromoquinolin-4-yl)oxy]cyclohexylamine (321 mg, 1.0 mmol), and 5-methylisoxazole-3-carboxylic acid (153 mg, 1.2 mmol) were put in pyridine (4.0 mL) and propanephosphonic acid cycloanhydride (637 mg, 2.0 mmol) was added. The reaction mixture was stirred overnight at room temperature. Water was added until a precipitate formed. After a further 10 minutes the precipitate was filtered off with suction and washed with water. After drying, the desired compound was obtained at 92% yield (400 mg).

$^1$H NMR (300 MHz, CDCl3) δ [ppm] 1.50-1.62 (m, 2H), 1.78-1.95 (m, 2H), 2.23-2.45 (m, 4H), 2.52 (s, 3H), 4.08-4.25 (br m, 1H), 4.50-4.68 (br m, 1H), 5.98 (d, 1H), 6.42 (s, 1H), 6.79 (d, 1H), 7.38 (t, 1H), 8.08 (d, 1H), 8.20 (d, 1H), 8.86 (d, 1H)

Example 3
N-[trans-4-(4-quinolyloxy)cyclohexyl]-3,4-difluorobenzamide

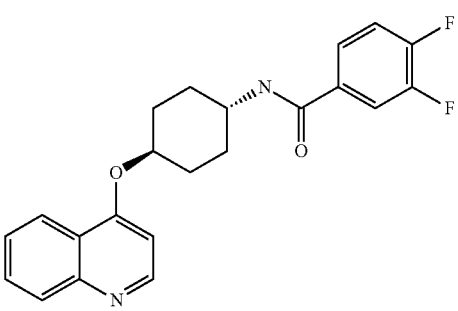 [SMILES: O=C(N[C@H]1CC[C@H](Oc2ccnc3ccccc23)CC1)c1ccc(F)c(F)c1]

trans-4-(4-Quinolyloxy)cyclohexylamine (400 mg, 1.65 mmol) was put in pyridine (12 mL) and catalytic amounts of triethylamine were added. At 0° C., 3,4-difluorobenzoyl chloride (291 mg, 1.65 mmol) was added. Then the reaction mixture was stirred at room temperature overnight. Water was added, and the precipitate was filtered off with suction. After drying, the desired product was obtained at 96% yield (610 mg).

$^1$H NMR (300 MHz, DMSO-d6) δ [ppm] 1.48-1.70 (m, 4H), 1.88-2.04 (m, 2H), 2.15-2.30 (m, 2H), 3.80-3.95 (m, 1H), 4.60-4.72 (m, 1H), 7.11 (d, 1H), 7.45-7.56 (m, 2H), 7.65-7.78 (m, 2H), 7.84-7.93 (m, 2H), 8.11 (d, 1H), 8.48 (d, 1H), 8.67 (d, 1H)

The following compounds according to the invention in Table 3 were prepared similarly.

TABLE 3

| Example | Structure | Analysis data | Yield |
|---|---|---|---|
| 4 | 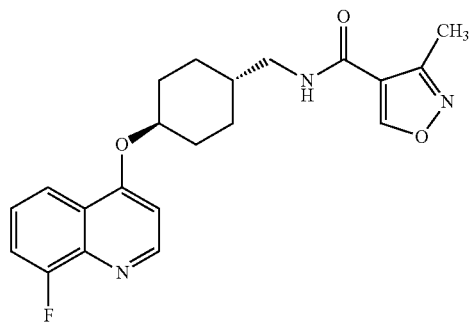 [SMILES: Cc1nocc1C(=O)NC[C@H]1CC[C@H](Oc2ccnc3c(F)cccc23)CC1]<br>N-({trans-4-[(8-fluoroquinolin-4-yl)oxy]cyclohexyl}methyl)-3-methylisoxazole-4-carboxamide | $^1$H NMR (400 MHz, DMSO-d$_6$) δ [ppm] 1.13-1.27 (m, 2 H), 1.44-1.65 (m, 3 H), 1.79-1.90 (m, 2 H), 2.13-2.23 (m, 2 H), 2.35 (s, 3 H), 3.10 (t, 2 H), 4.73-4.85 (m, 1 H), 7.36 (d, 1 H), 7.56-7.63 (m, 1 H), 7.66-7.74 (m, 1 H), 7.98 (d, 1 H), 8.32 (t, 1 H), 8.83 (d, 1 H), 9.21 (s, 1 H) | 17% (reaction with HATU, carboxylic acid) in DMF |
| 5 | 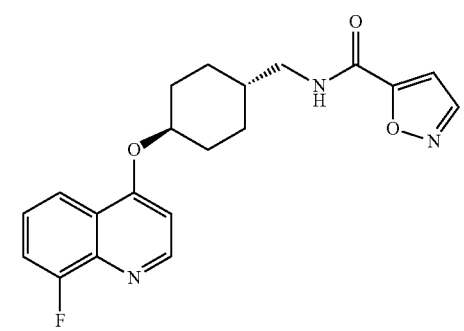 [SMILES: O=C(NC[C@H]1CC[C@H](Oc2ccnc3c(F)cccc23)CC1)c1ccno1]<br>N-({trans-4-[(8-fluoroquinolin-4-yl)oxy]cyclohexyl}methyl)-isoxazole-5-carboxamide | $^1$H NMR (400 MHz, DMSO-d$_6$) δ [ppm] 1.15-1.28 (m, 2 H), 1.44-1.58 (m, 2 H), 1.58-1.71 (m, 1 H), 1.78-1.87 (m, 2 H), 2.14-2.22 (m, 2 H), 3.15 (t, 2 H), 4.75-4.85 (m, 1 H), 7.03 (d, 1 H), 7.37 (d, 1 H), 7.54-7.64 (m, 1 H), 7.66-7.74 (m, 1 H), 7.98 (d, 1 H), 8.70 (d, 1 H), 8.83 (d, 1 H), 8.96 (t, 1 H) | 11% (reaction with HATU, carboxylic acid) in DMF |
| 6 | 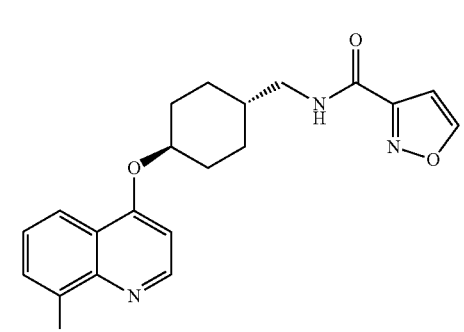<br>N-({trans-4-[(8-fluoroquinolin-4-yl)oxy]cyclohexyl}methyl)isoxazole-3-carboxamide | $^1$H NMR (300 MHz, DMSO-d$_6$) δ [ppm] 1.09-1.27 (m, 2 H), 1.38-1.54 (m, 2 H), 1.57-1.72 (m, 1 H), 1.76-1.86 (m, 2 H), 2.12-2.25 (m, 2 H), 3.14 (t, 2 H), 4.58-4.70 (m, 1 H), 6.85 (d, 1 H), 7.17 (d, 1 H), 7.42-7.56 (m, 2 H), 7.89 (d, 1 H), 8.69 (d, 1 H), 8.81 (t, 1 H), 9.04 (d, 1 H) | 46% (reaction with HATU, carboxylic acid) in THF |

TABLE 3-continued

| Example | Structure | Analysis data | Yield |
|---|---|---|---|
| 7 | 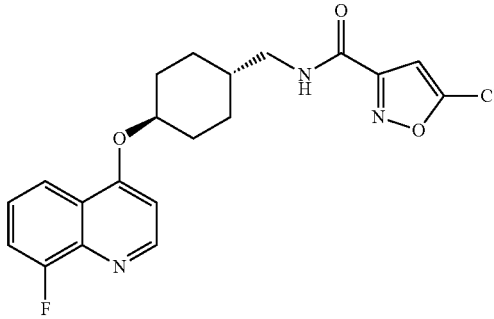<br>N-({trans-4-[(8-fluoroquinolin-4-yl)oxy]cyclohexyl}methyl)-5-methylisoxazole-3-carboxamide | $^1$H NMR (300 MHz, DMSO-d$_6$) δ [ppm] 1.09-1.26 (m, 2 H), 1.38-1.69 (m, 3 H), 1.74-1.88 (m, 2 H), 2.09-2.26 (m, 2 H), 2.42 (s, 3H), 3.12 (t, 2 H), 4.68-4.81 (m, 1 H), 6.49 (d, 1 H), 7.30 (d, 1 H), 7.49-7.70 (m, 2 H), 7.95 (d, 1 H), 8.71 (t, 1 H), 8.78 (d, 1 H) | 56% (reaction with HATU, carboxylic acid) in DMF |
| 8 | 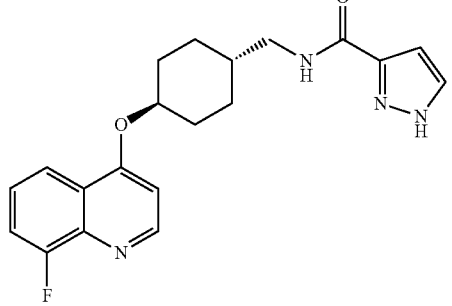<br>N-({trans-4-[(8-fluoroquinolin-4-yl)oxy]cyclohexyl}methyl)-1H-pyrazole-3-carboxamide | $^1$H NMR (400 MHz, DMSO-d$_6$) δ [ppm] 1.13-1.28 (m, 2 H), 1.45-1.69 (m, 3 H), 1.76-1.86 (m, 2 H), 2.14-2.22 (m, 2 H), 3.13 (t, 2 H), 4.77-4.87 (m, 1 H), 6.62 (d, 1 H), 7.41 (d, 1 H), 7.57-7.65 (m, 1 H), 7.69-7.77 (m, 2 H), 8.00 (d, 1 H), 8.16 (t, 1 H), 8.85 (d, 1 H) | 14% (reaction with HATU, carboxylic acid) DMF |
| 9 | 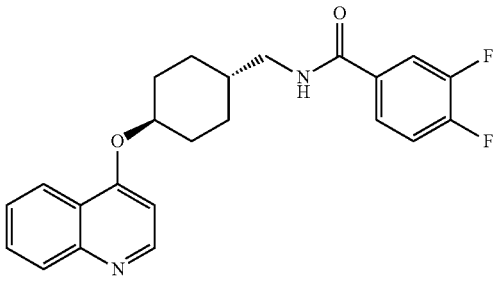 [SMILES: O=C(NC[C@H]1CC[C@H](Oc2ccnc3ccccc23)CC1)c1ccc(F)c(F)c1]<br>N-{[trans-4-(4-quinolyloxy)cyclohexyl]methyl}-3,4-difluorobenzamide | $^1$H NMR (400 MHz, DMSO-d$_6$) δ [ppm] 1.15-1.26 (m, 2 H), 1.41-1.53 (m, 2 H), 1.57-1.69 (m, 1 H), 1.79-1.88 (m, 2 H), 2.13-2.24 (m, 2 H), 3.16 (t, 2 H), 4.57-4.67 (m, 1 H), 7.05 (d, 1 H), 7.46-7.56 (m, 2 H), 7.65-7.76 (m, 2 H), 7.83-7.91 (m, 2 H), 8.09 (dd, 1 H), 8.56 (t, 1 H), 8.65 (d, 1 H) | 57% (reaction with HATU, carboxylic acid) in THF |
| 10 | 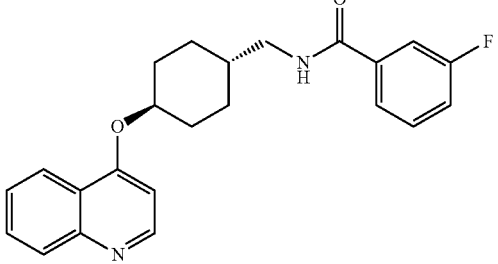<br>N-{[trans-4-(4-quinolyloxy)cyclohexyl]methyl}-3-fluorobenzamide | $^1$H NMR (500 MHz, DMSO-d$_6$) δ [ppm] 1.19-1.29 (m, 2 H), 1.45-1.58 (m, 2 H), 1.64-1.73 (m, 1 H), 1.85-1.92 (m, 2 H), 2.19-2.27 (m, 2 H), 3.21 (t, 2 H), 4.61-4.69 (m, 1 H), 7.09 (d, 1 H), 7.38 (td, 1 H), 7.49-7.55 (m, 2 H), 7.64-7.74 (m, 3 H), 7.92 (d, 1 H), 8.13 (dd, 1 H), 8.61 (t, 1 H), 8.69 (d, 1 H) | 52% (reaction with HATU, carboxylic acid) in THF |

TABLE 3-continued

| Example | Structure | Analysis data | Yield |
|---|---|---|---|
| 11 | N-{[trans-4-(4-quinolyloxy)cyclohexyl]methyl}-5-methylisoxazole-3-carboxamide | $^1$H NMR (300 MHz, DMSO-d$_6$) δ [ppm] 1.09-1.25 (m, 2 H), 1.40-1.53 (m, 2 H), 1.55-1.68 (m, 1 H), 1.74-1.85 (m, 2 H), 2.12-2.22 (m, 2 H), 2.42 (s, 3 H), 3.12 (t, 2 H), 4.55-4.67 (m, 1 H), 6.49 (d, 1H), 7.05 (d, 1 H), 7.49 (ddd, 1 H), 7.68 (ddd, 1 H), 7.88 (d, 1 H), 8.08 (d, 1 H), 8.65 (d, 1 H), 8.71 (t, 1 H) | 47% (reaction with carboxylic acid chloride in DMF) |
| 12 | N-{trans-4-[(8-bromoquinolin-4-yl)oxy]cyclohexyl}-3-fluorobenzamide | $^1$H NMR (300 MHz, DMSO-d$_6$) δ [ppm] 1.50-1.70 (m, 4 H), 1.89-2.00 (m, 2 H), 2.16-2.29 (m, 2 H), 3.81-3.94 (m, 1 H), 4.63-4.76 (m, 1 H), 7.24 (d, 1 H), 7.29-7.54 (m, 3 H), 7.59-7.71 (m, 2 H), 8.08 (dd, 1 H), 8.15 (dd, 1 H), 8.36 (d, 1 H), 8.78 (d, 1 H) | 98% (reaction with HATU, carboxylic acid) in THF |
| 13 | N-{trans-4-[(8-bromoquinolin-4-yl)oxy]cyclohexyl}-3,4-difluorobenzamide | $^1$H NMR (400 MHz, CDCl$_3$) δ [ppm] 1.48-1.65 (m, 2 H), 1.78-1.92 (m, 2 H), 2.25-2.40 (m, 4 H), 4.05-4.18 (br m, 1 H), 4.52-4.62 (br m, 1 H), 5.98 (d, 1 H), 6.85 (d, 1 H), 7.19-7.25 (m, 1 H), 7.50-7.60 (m, 2 H), 7.65 (t, 1 H), 8.12 (d, 1 H), 8.46 (d, 1 H), 8.90 (d, 1 H) | 87% (reaction with carboxylic acid chloride in pyridine) |

TABLE 3-continued

| Example | Structure | Analysis data | Yield |
|---|---|---|---|
| 14 | 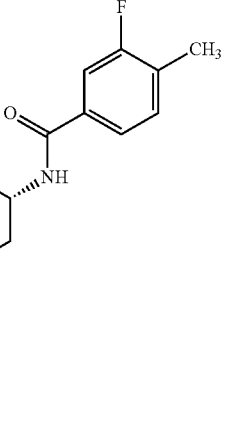<br>N-{trans-4-[(8-bromoquinolin-4-yl)oxy]cyclohexyl}-3-fluoro-4-methylbenzamide | $^1$H NMR (300 MHz, CDCl$_3$) δ [ppm] 1.40-1.58 (m, 2 H), 1.75-1.91 (m, 2 H), 2.20-2.38 (m, 4 H), 2.36 (s, 3 H), 4.05-4.20 (br m, 1 H), 4.48-4.62 (br m, 1 H), 5.95 (d, 1 H), 6.80 (d, 1 H), 7.20-7.50 (ser m, 4 H), 8.04 (d, 1 H), 8.21 (d, 1 H), 8.88 (d, 1 H) | 87% (reaction with carboxylic acid chloride in pyridine) |
| 15 | 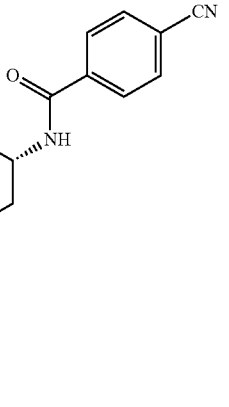<br>N-{trans-4-[(8-bromoquinolin-4-yl)oxy]cyclohexyl}-4-cyanobenzamide | $^1$H NMR (300 MHz, CDCl$_3$) δ [ppm] 1.45-1.60 (m, 2 H), 1.75-1.92 (m, 2 H), 2.20-2.42 (m, 4 H), 4.06-4.22 (br m, 1 H), 4.48-4.65 (br m, 1 H), 6.10 (d, 1 H), 6.80 (d, 1 H), 7.36 (t, 1 H), 7.75 (d, 2 H), 7.90 (d, 2 H), 8.05 (d, 1 H), 8.22 (d, 1 H), 8.88 (d, 1 H) | 85% (reaction with carboxylic acid chloride in pyridine) |
| 16 | 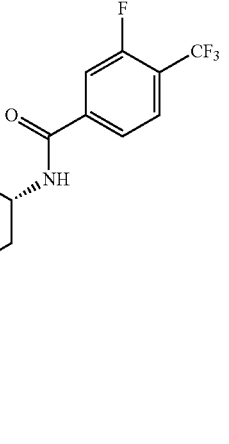<br>N-{trans-4-[(8-bromoquinolin-4-yl)oxy]cyclohexyl}-3-fluoro-4-(trifluoromethyl)benzamide | $^1$H NMR (300 MHz, DMSO-d$_6$) δ [ppm] 1.50-1.72 (m, 4 H), 1.90-2.05 (m, 2 H), 2.15-2.31 (m, 2 H), 3.80-3.97 (m, 1 H), 4.64-4.78 (m, 1 H), 7.26 (d, 1 H), 7.46 (t, 1 H), 7.80-7.98 (m, 3 H), 8.08 (d, 1 H), 8.14 (d, 1 H), 8.61 (d, 1 H), 8.78 (d, 1 H) | 10% (reaction with carboxylic acid chloride in pyridine) |

TABLE 3-continued

| Example | Structure | Analysis data | Yield |
|---|---|---|---|
| 17 | 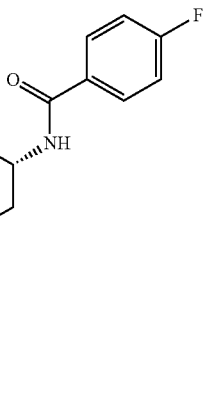 N-{trans-4-[(8-bromoquinolin-4-yl)oxy]cyclohexyl}-4-fluorobenzamide | $^1$H NMR (600 MHz, CDCl$_3$) δ [ppm] 1.45-1.56 (m, 2 H), 1.78-1.89 (m, 2 H), 2.25-2.40 (m, 4 H), 4.08-4.20 (br m, 1 H), 4.48-4.60 (br m, 1 H), 5.96 (d, 1 H), 6.80 (d, 1 H), 7.10-7.15 (m, 2 H), 7.35 (t, 1 H), 7.76-7.81 (m, 2 H), 8.04 (dd, 1 H), 8.22 (dd, 1 H), 8.86 (d, 1 H) | 81% (reaction with carboxylic acid chloride in pyridine) |
| 18 | 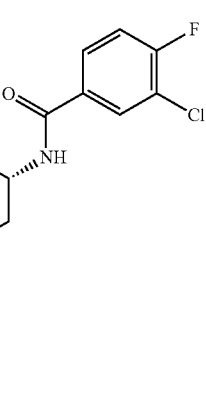 N-{trans-4-[(8-bromoquinolin-4-yl)oxy]cyclohexyl}-3-chloro-4-fluorobenzamide | $^1$H NMR (300 MHz, DMSO-d$_6$) δ [ppm] 1.48-1.72 (m, 4 H), 1.88-2.05 (m, 2 H), 2.12-2.30 (m, 2 H), 3.76-3.95 (m, 1 H), 4.61-4.78 (m, 1 H), 7.25 (d, 1 H), 7.48-7.55 (m, 2 H), 7.82-7.92 (m, 1 H), 8.02-8.10 (m, 2 H), 8.16 (d, 1 H), 8.45 (d, 1 H), 8.78 (d, 1 H) | 86% (reaction with carboxylic acid chloride in pyridine) |
| 19 | 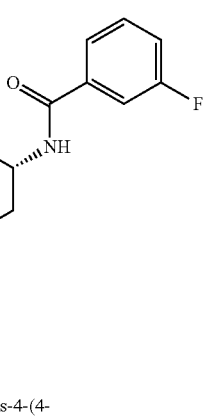 N-{trans-4-(4-quinolyloxy)cyclohexyl}-3-fluorobenzamide | $^1$H NMR (300 MHz, DMSO-d$_6$) δ [ppm] 1.50-1.70 (m, 4 H), 1.88-2.02 (m, 2 H), 2.18-2.30 (m, 2 H), 3.80-3.98 (m, 1 H), 4.59-4.72 (m, 1 H), 7.11 (d, 1 H), 7.30-7.75 (ser m, 6 H), 7.90 (d, 1 H), 8.11 (d, 1 H), 8.38 (d, 1 H), 8.68 (d, 1 H) | 84% (reaction with carboxylic acid chloride in pyridine) |

TABLE 3-continued

| Example | Structure | Analysis data | Yield |
|---|---|---|---|
| 20 | 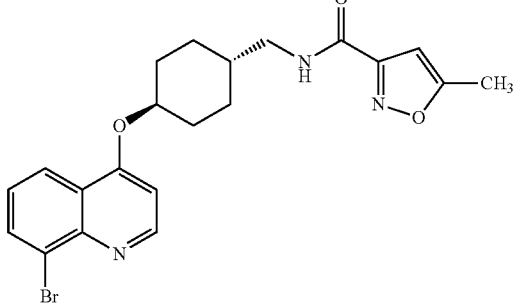<br>N-({trans-4-[(8-bromoquinolin-4-yl)oxy]cyclohexyl}methyl)-5-methylisoxazole-3-carboxamide | $^1$H NMR (300 MHz, CDCl$_3$) δ [ppm] 1.19-1.36 (m, 2 H), 1.53-1.82 (m, 3 H), 1.93-2.07 (m, 2 H), 2.24-2.40 (m, 2 H), 2.50 (s, 3 H), 3.30-3.45 (m, 2 H), 4.42-4.58 (br m, 1 H), 6.45 (s, 1 H), 6.78 (d, 1 H), 6.88 (t, 1 H), 7.31 (t, 1 H), 8.03 (d, 1 H), 8.20 (d, 1 H), 8.85 (d, 1H) | 73% (reaction with T3P in pyridine) |
| 21 | 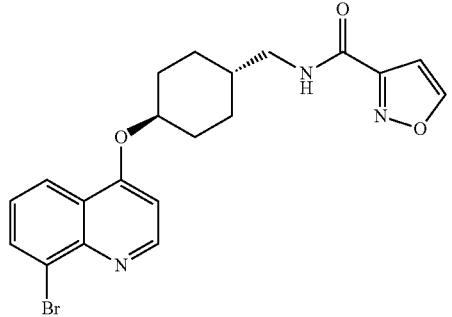 [SMILES: O=C(NC[C@H]1CC[C@H](Oc2ccnc3c(Br)cccc23)CC1)c1ccon1]<br>N-({trans-4-[(8-bromoquinolin-4-yl)oxy]cyclohexyl}methyl)isoxazole-3-carboxamide | $^1$H NMR (300 MHz, CDCl$_3$) δ [ppm] 1.20-1.32 (m, 2 H), 1.57-1.82 (m, 3 H), 1.95-2.10 (m, 2 H), 2.28-2.38 (m, 2 H), 3.44 (t, 2 H), 4.44-4.55 (br m, 1 H), 6.79 (d, 1 H), 6.85 (s, 1 H), 6.93 (t, 1 H), 7.32 (t, 1 H), 8.04 (dd, 1 H), 8.20 (dd, 1 H), 8.50 (s, 1 H), 8.86 (d, 1 H) | 58% (reaction with T3P in pyridine) |
| 22 | 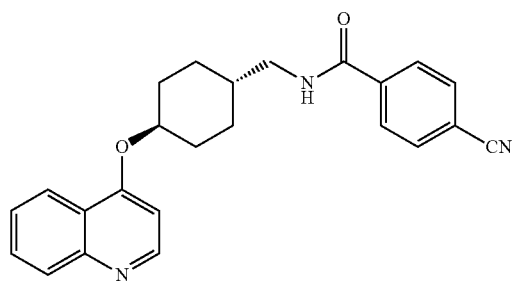 [SMILES: N#Cc1ccc(C(=O)NC[C@H]2CC[C@H](Oc3ccnc4ccccc34)CC2)cc1]<br>N-{[trans-4-(4-quinolyloxy)cyclohexyl]methyl}-4-cyanobenzamide | $^1$H-NMR (300 MHz, CDCl$_3$): δ [ppm] 1.53-1.85 (m, 5H), 1.94-2.03 (m, 2H), 2.26-2.39 (m, 2H), 3.43 (t, 2H), 4.42-4.56 (m, 1H), 6.33 (t, 1H), 6.72 (d, 1H), 7.48 (t, 1H), 7.68 (t, 1H), 7.76 (d, 2H), 7.89 (d, 2H), 8.01 (d, 1H), 8.20 (d, 1H), 8.71 (d, 1H). | 26% (reaction with carboxylic acid chloride in pyridine) |

Example 23

N-{trans-4-[(8-cyanoquinolin-4-yl)oxy]cyclohexyl}-3-fluorobenzamide

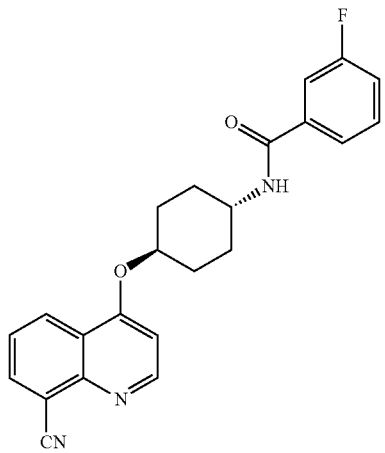 [SMILES: N#Cc1cccc2c(O[C@H]3CC[C@H](NC(=O)c4cccc(F)c4)CC3)ccnc12]

N-{trans-4-[(8-Bromoquinolin-4-yl)oxy]cyclohexyl}-3-fluorobenzamide (500 mg, 1.13 mmol) (see example 12), sodium carbonate (120 mg, 1.13 mmol) and palladium(II) acetate (13 mg, 0.06 mmol) were dissolved in N,N-dimethylacetamide (23 mL) and finely triturated potassium hexacyanoferrate (105 mg, 2.5 mmol) was added. The reaction mixture was stirred under a nitrogen atmosphere for 3 hours at 120° C. After cooling to room temperature, the reaction mixture was diluted with water and saturated sodium chloride solution and extracted with ethyl acetate. The combined organic phases were dried over sodium sulphate, then the sodium sulphate and solvent residues were removed. After chromatography of the residue, the desired product was obtained at 43% yield (190 mg).

$^1$H NMR (300 MHz, DMSO-$d_6$) δ [ppm] 1.50-1.70 (m, 4H), 1.90-2.01 (m, 2H), 2.17-2.29 (m, 2H), 3.80-3.94 (m, 1H), 4.67-4.79 (m, 1H), 7.33 (d, 2H), 7.44-7.53 (m, 1H), 7.59-7.71 (m, 3H), 8.31 (dd, 1H), 8.36-8.45 (m, 2H), 8.85 (d, 1H).

The following compounds according to the invention in Table 4 were prepared similarly:

TABLE 4

| Example | Structure | Analysis data | Yield |
| --- | --- | --- | --- |
| 24 | N-{trans-4-[(8-cyanoquinolin-4-yl)oxy]cyclohexyl}-3,4-difluorobenzamide | $^1$H NMR (400 MHz, CDCl$_3$) δ [ppm] 1.48-1.65 (m, 2 H), 1.78-1.92 (m, 2 H), 2.25-2.40 (m, 4 H), 4.05-4.18 (br m, 1 H), 4.52-4.62 (br m, 1 H), 5.98 (d, 1 H), 6.85 (d, 1 H), 7.19-7.25 (m, 1 H), 7.50-7.60 (m, 2 H), 7.65 (t, 1 H), 8.12 (d, 1 H), 8.46 (d, 1 H), 8.90 (d, 1 H) | 38% |
| 25 | N-{trans-4-[(8-cyanoquinolin-4-yl)oxy]cyclohexyl}-4-fluorobenzamide | $^1$H NMR (300 MHz, CDCl$_3$) δ [ppm] 1.46-1.60 (m, 2 H), 1.80-1.90 (m, 2 H), 2.25-2.40 (m, 4 H), 4.08-4.20 (br m, 1 H), 4.52-4.65 (br m, 1 H), 6.02 (d, 1 H), 6.88 (d, 1 H), 7.22 (t, 1 H), 7.40-7.63 (ser m, 4 H), 8.10 (d, 1 H), 8.48 (d, 1 H), 8.90 (d, 1 H) | 43% |

TABLE 4-continued

| Example | Structure | Analysis data | Yield |
|---|---|---|---|
| 26 | 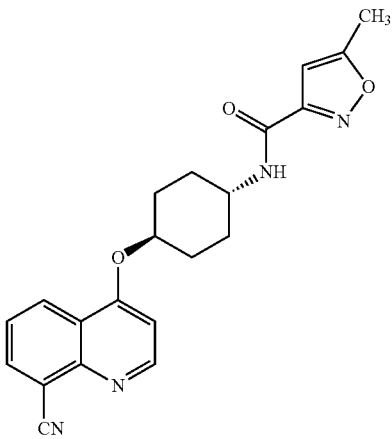<br>N-{trans-4-[(8-cyanoquinolin-4-yl)oxy)cyclohexyl}-5-methylisoxazole-3-carboxamide | $^1$H NMR (300 MHz, DMSO-d$_6$) δ [ppm] 1.50-1.70 (m, 4 H), 1.82-1.98 (m, 2 H), 2.10-2.30 (m, 2 H), 2.41 (s, 3 H), 3.75-3.94 (br m, 1 H), 4.60-4.80 (br m, 1 H), 6.50 (s, 1, H), 7.30 (d, 1 H), 7.65 (t, 1 H), 8.30 (d, 1 H), 8.40 (d, 1 H), 8.62 (d, 1 H), 8.85 (d, 1 H) | 16% |
| 27 | 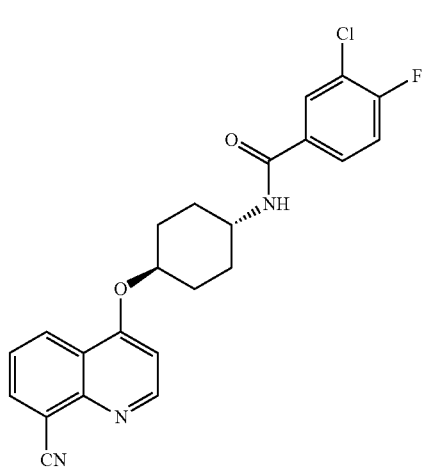 [SMILES: N#Cc1cccc2c(O[C@H]3CC[C@H](NC(=O)c4ccc(F)c(F)c4)CC3)ccnc12]<br>3-chloro-N-{trans-4-[(8-cyanoquinolin-4-yl)oxy]cyclohexyl}-4-fluorobenzamide | $^1$H NMR (300 MHz, DMSO-d$_6$) δ [ppm] 1.48-1.72 (m, 4 H), 1.88-2.04 (m, 2 H), 2.12-2.30 (m, 2 H), 3.80-3.94 (br m, 1 H), 4.67-4.80 (br m, 1 H), 7.33 (d, 1 H), 7.50 (t, 1 H), 7.68 (t, 1 H), 7.82-7.91 (m, 1 H), 8.06 (dd, 1 H), 8.30 (dd, 1 H), 8.38-8.48 (m, 2 H), 8.86 (d, 1 H) | 38% |
| 28 | 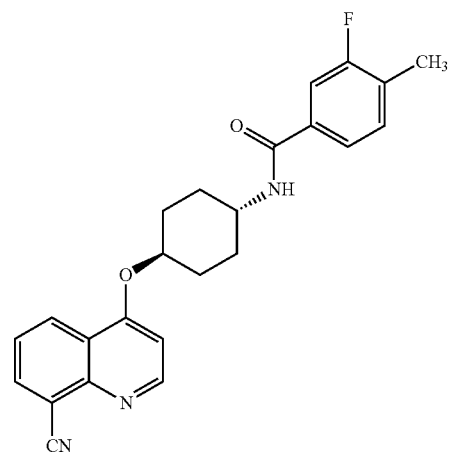 [SMILES: Cc1ccc(C(=O)N[C@H]2CC[C@H](Oc3ccnc4c(C#N)cccc34)CC2)cc1F]<br>N-{trans-4-[(8-cyanoquinolin-4-yl)oxy]cyclohexyl}-3-fluoro-4-methylbenzamide | $^1$H NMR (300 MHz, CDCl$_3$) δ [ppm] 1.44-1.58 (m, 2 H), 1.75-1.95 (m, 2 H), 2.24-2.44 (m, 4 H), 2.35 (s, 3 H), 4.05-4.20 (br m, 1 H), 4.52-4.65 (br m, 1 H), 5.95 (d, 1 H), 6.88 (d, 1 H), 7.20-7.35 (m, 1 H), 7.40-7.51 (m, 2 H), 7.60 (t, 1 H), 8.10 (dd, 1 H), 8.48 (d, 1 H), 8.90 (d, 1 H) | 51% |

TABLE 4-continued

| Example | Structure | Analysis data | Yield |
|---|---|---|---|
| 29 | 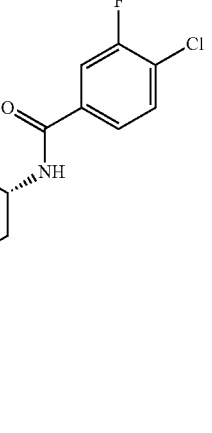<br>4-chloro-N-{trans-4-[(8-cyanoquinolin-4-yl)oxy]cyclohexyl}-3-fluorobenzamide | $^1$H NMR (300 MHz, DMSO-d$_6$) δ [ppm] 1.48-1.72 (m, 4 H), 1.88-2.04 (m, 2 H), 2.12-2.30 (m, 2 H), 3.80-3.94 (br m, 1 H), 4.67-4.80 (br m, 1 H), 7.33 (d, 1 H), 7.50 (t, 1 H), 7.68 (t, 1 H), 7.82-7.91 (m, 1 H), 8.06 (dd, 1 H), 8.30 (dd, 1 H), 8.38-8.48 (m, 2 H), 8.86 (d, 1 H) | 35% |
| 30 | 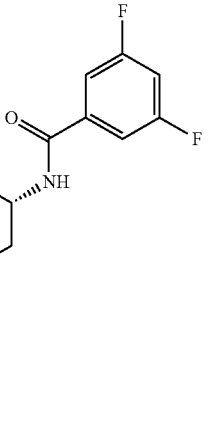<br>N-{trans-4-[(8-cyanoquinolin-4-yl)oxy]cyclohexyl}-3,5-difluorobenzamide | $^1$H NMR (300 MHz, DMSO-d$_6$) δ [ppm] 1.52-1.70 (m, 4 H), 1.92-2.02 (m, 2 H), 2.18-2.30 (m, 2 H), 3.80-3.94 (br m, 1 H), 4.68-4.80 (br m, 1 H), 7.32 (d, 1 H), 7.39-7.48 (m, 1 H), 7.52-7.60 (m, 2 H), 7.68 (t, 1 H), 8.30 (d, 1 H), 8.38-8.48 (m, 2 H), 8.85 (d, 1 H) | 41% |
| 31 | 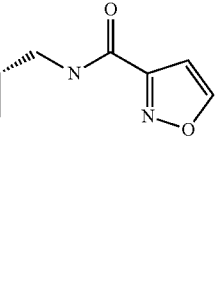<br>N-({trans-4-[(8-cyanoquinolin-4-yl)oxy]cyclohexyl}methyl)isoxazole-3-carboxamide | $^1$H NMR (400 MHz, CDCl$_3$) δ [ppm] 1.20-1.38 (m, 2 H), 1.53-1.85 (m, 3 H), 1.96-2.12 (m, 2 H), 2.27-2.42 (m, 2 H), 3.38-3.34 (m, 1 H), 4.48-4.60 (br m, 1 H), 6.80-6.90 (m, 2 H), 6.95 (t, 1H), 7.52 (t, 1 H), 8.08 (dd, 1 H), 8.42 (dd, 1 H), 8.48 (s, 1 H), 8.87 (d, 1 H) | |

TABLE 4-continued

| Example | Structure | Analysis data | Yield |
|---|---|---|---|
| 32 | N-({trans-4-[(8-cyanoquinolin-4-yl)oxy]cyclohexyl}methyl)-5-methylisoxazole-3-carboxamide | $^1$H NMR (300 MHz, CDCl$_3$) δ [ppm] 1.18-1.35 (m, 2 H), 1.50-1.82 (m, 3 H), 1.94-2.08 (m, 2 H), 2.25-2.38 (m, 2 H), 2.50 (s, 3 H), 3.36 (t, 2 H), 4.45-4.58 (m, 1 H), 6.46 (s, 1 H), 6.84 (d, 1 H), 6.89 (t, 1 H), 7.53 (t, 1 H), 8.08 (dd, 1 H), 8.44 (dd, 1 H), 8.88 (d, 1 H) | |

Pharmacological Characterization of the Compounds According to the Invention

Transactivation Assay for the Wild-Type Androgen Receptor

For determining the androgen receptor-dependent transcription, a cellular assay system was used, consisting of PC-3 cells (Kaighn et al., Invest. Urol. 17: 16-23, 1979), which express the human androgen receptor stably and recombinantly (full length, wild-type form, see Swiss-Prot Acc. No. P10275, Entry Version 159, Sequence Version 2). In addition, these PC3 cells contain a stably integrated reporter gene plasmid, which is based on the commercially available plasmid pGL4.14 (#E6691, Promega Corporation, Madison, Wis., USA) and contains the luciferase gene from the American firefly (*Photinus pyralis*) under the control of the MMTV promoter (Cato et al., EMBO J. 6: 363-368, 1987). These cells were propagated in routine cell culture at 37° C. and 5% CO$_2$ in a medium containing 90% RPMI 1640 (Invitrogen GmbH, Darmstadt, Germany), 100 U penicillin, 100 µg/ml streptomycin (Invitrogen), 4 mM L-glutamine (Invitrogen), 10% fetal calf serum (FCS Serum Gold, PAA Laboratories GmbH, Cölbe, Germany), 600 µg/ml Geneticin (G418-sulphate, Invitrogen) and 10 µg/ml puromycin (Sigma Aldrich GmbH, Germany).

For carrying out the transactivation assays, approx. 1000 cells per well were plated out in a 384-well cell culture plate in a medium that contained activated charcoal-treated calf serum (FCS Serum Gold, PAA Laboratories) at a concentration of 5% (v/v). The test substances were added in a concentration series from $5.12 \times 10^{-12}$ to $1 \times 10^{-5}$ M in the presence of $1 \times 10^{-10}$ R1881 (methyltrienolone). The test plates were incubated overnight at 37° C. and 5% CO$_2$. After 16 hours, 15 µl of Steady Glo Lysis and Detection reagent (E2550, Promega Corporation, Madison, Wis., USA) was added per well and the luminescence was read in a Topcount Luminometer (PerkinElmer, Waltham, Mass., USA) for 4 seconds per well. The luminescence values obtained were normalized, wherein 100% corresponded to the effect of the unstimulated control (without R1881), and 0% corresponded to the effect of the stimulated control (R1881 plus DMSO instead of test substance). The IC$_{50}$ value was determined by regression analysis based on a four-parameter equation (minimum, maximum, IC$_{50}$, Hill coefficient; Y=Max+(Min−Max)/(1+(X/IC$_{50}$)$^{Hill}$)).

For the compounds according to the invention, using this assay the following IC$_{50}$ values were determined with respect to the wild-type androgen receptor:

| Example | IC$_{50}$ (µM) |
|---|---|
| 1 | 0.24 |
| 2 | 0.020 |
| 3 | 0.045 |
| 4 | 0.21 |
| 5 | 0.46 |
| 6 | 0.74 |
| 7 | 0.48 |
| 8 | 0.42 |
| 9 | 0.105 |
| 10 | 0.194 |
| 11 | 0.21 |
| 12 | 0.093 |
| 13 | 0.170 |
| 14 | 0.068 |
| 15 | 0.261 |
| 16 | 0.463 |
| 17 | 0.477 |
| 18 | 0.190 |
| 19 | 0.032 |
| 20 | 0.69 |
| 21 | 0.63 |
| 22 | 0.330 |
| 23 | 0.052 |
| 24 | 0.092 |
| 25 | 0.140 |
| 26 | 0.018 |
| 27 | 0.067 |
| 28 | 0.045 |
| 29 | 0.061 |
| 30 | 0.039 |
| 31 | 0.72 |
| 32 | 0.65 |

Transactivation Assay for the Androgen Receptor Mutant W741C

PC-3 cells (Kaighn et al., Invest. Urol. 17: 16-23, 1979) were plated out at a density of 10000 cells per well of a 96-well cell culture plate in RPMI 1640 medium (F1235, Biochrom AG, Berlin, Germany), which contained activated charcoal-treated calf serum (FCS Serum Gold, PAA Laboratories) at a concentration of 5% (v/v). On the next day the cells were transiently transfected with the pSG5-vector (#216201 Stratagene), which contained the sequence of the androgen receptor mutant W741C (Haapala et al., Lab Invest. 81(12): 1647-51, 2001), and with a reporter plasmid based on pGL4.14 (#E6691, Promega) with the luciferase-gene (from *Photinus pyralis*) under the control of the MMTV promoter (Cato et al., EMBO J. 6: 363-8, 1987). The cells were treated with the test substances in concentrations from $1\times10^{-8}$ to $1\times10^{-10}$ M in the presence of $1\times10^{-10}$ M R1881 and were incubated overnight at 37° C. and 5% $CO_2$. After 24 hours, 100 µl of Steady Glo Lysis and Detection reagent (E2550, Promega) was added per well and the luminescence was read in a Victor3 Luminometer (PerkinElmer) for 1 second per well. The luminescence values obtained were normalized, wherein 100% corresponded to the effect of the unstimulated control (without R1881), and 0% corresponded to the effect of the stimulated control (R1881 plus DMSO instead of test substance). The $IC_{50}$ value was determined by regression analysis based on a four-parameter equation (minimum, maximum, $IC_{50}$, Hill coefficient; $Y=Max+(Min-Max)/(1+(X/IC_{50})^{Hill}))$.

For selected compounds according to the invention, the following $IC_{50}$ values were found using this assay:

| Example | $IC_{50}$ (µM) |
|---|---|
| 9 | 0.072 |
| 10 | 0.220 |
| 23 | 0.030 |
| 24 | 0.072 |

Transactivation Assay for the Androgen Receptor Mutant E709Y

PC-3 cells (Kaighn et al., Invest. Urol. 17: 16-23, 1979) were plated out at a density of 10000 cells per well of a 96-well cell culture plate in RMPI 1640 medium (F1235, Biochrom AG Berlin, Germany) that contained activated charcoal-treated calf serum (FCS Serum Gold, PAA Laboratories) at a concentration of 5% (v/v). On the next day the cells were transiently transfected with the pSG5-vector (#216201 Stratagene), which contained the sequence of the androgen receptor mutant E709Y (Georget et al., Mol. Endocrinol. 20(4): 724-734, 2006), and with the MMTV-luciferase plasmid (see above, transactivation assay for the androgen receptor mutant W741C). The cells were treated with the test substances in concentrations from $1\times10^{-8}$ to $1\times10^{-10}$ M in the presence of $1\times10^{-10}$ M R1881 and were incubated overnight at 37° C. and 5% $CO_2$. After 24 hours, 100 µl of Steady Glo Lysis and Detection reagent (E2550, Promega) was added per well and the luminescence was read in a Victor3 Luminometer (PerkinElmer) for 1 second per well. The luminescence values obtained were normalized, wherein 100% corresponded to the effect of the unstimulated control (without R1881), and 0% corresponded to the effect of the stimulated control (R1881 plus DMSO instead of test substance). The $IC_{50}$ value was determined by regression analysis based on a four-parameter equation (minimum, maximum, $IC_{50}$, Hill coefficient; $Y=Max+(Min-Max)/(1+(X/IC_{50})^{Hill}))$.

For selected compounds according to the invention, the following $IC_{50}$ values were found using this assay:

| Example | $IC_{50}$ (µM) |
|---|---|
| 9 | 0.056 |
| 10 | 0.175 |
| 23 | 0.009 |
| 24 | 0.014 |

Proliferation Assay with LNCaP Cells

LNCaP cells (Horoszewicz et al., in "Models for Prostate Cancer" (ed. G. P. Murphy), Alan R. Liss, New York 1981, p. 115-132; Horoszewicz et al., Cancer Res. 43: 1809-1818, 1983) were plated out at a density of 2000 cells per well of a 96-well cell culture plate in RMPI 1640 medium (F1275, Biochrom AG), which contained activated charcoal-treated calf serum (FCS Serum Gold, PAA Laboratories) at a concentration of 5% (v/v). Three days later the cells were treated with the test substances in concentrations from $1\times10^{-8}$ to $1\times10^{-10}$ M in the presence of $1\times10^{-10}$ M R1881. Cell proliferation was determined seven days later after incubation for 2 hours with AlamarBlue (DAL1100, Invitrogen) (Nakayama et al., J Immunol Methods, 204(2): 205-8, 1997). The fluorescence values obtained were normalized, wherein 100% corresponded to the effect of the unstimulated control (without R1881), and 0% corresponded to the effect of the stimulated control (R1881 plus DMSO instead of test substance). The $IC_{50}$ value was determined by regression analysis based on a four-parameter equation (minimum, maximum, $IC_{50}$, Hill coefficient; $Y=Max+(Min-Max)/(1+(X/IC_{50})^{Hill}))$.

For selected compounds according to the invention, the following $IC_{50}$ values were found using this assay:

| Example | $IC_{50}$ (µM) |
|---|---|
| 1 | 0.17 |
| 3 | 0.099 |
| 4 | 0.25 |
| 5 | 0.39 |
| 6 | 0.021 |
| 7 | 0.097 |
| 8 | 1.12 |
| 11 | 0.26 |
| 15 | 0.19 |
| 19 | 0.11 |
| 22 | 0.087 |
| 23 | 0.028 |
| 25 | 0.233 |
| 28 | 0.051 |
| 29 | 0.029 |
| 30 | 0.030 |
| 31 | 0.73 |
| 32 | 0.56 |

Proliferation assay with LAPC-4 cells

LAPC-4 cells (Klein et al., Nat Med. 3(4): 402-8, 1997) were plated out at a density of 4000 cells per well of a 96-well cell culture plate in RMPI 1640 medium (F1275, Biochrom AG) that contained activated charcoal-treated calf serum (FCS Serum Gold, PAA Laboratories) at a concentration of 10% (v/v). On the next day the cells were treated with the test substances in concentrations from $1\times10^{-8}$ to $1\times10^{-10}$ M in the presence of $1\times10^{-9}$ M R1881. Cell proliferation was determined seven days later after incubation for 2 hours with AlamarBlue (DAL1100, Invitrogen) (Nakayama et al., J Immunol Methods, 204(2): 205-8, 1997). The fluorescence values obtained were normalized, wherein 100% corresponded to the effect of the unstimulated control (without R1881), and 0% corresponded to the effect of the stimulated control (R1881 plus DMSO instead of test substance). The $IC_{50}$ value was determined by regression analysis based on a four-parameter equation (minimum, maximum, $IC_{50}$, Hill coefficient; $Y=Max+(Min-Max)/(1+(X/IC_{50})^{Hill}))$.

For selected compounds according to the invention, the following $IC_{50}$ values were found using this assay:

| Example | $IC_{50}$ (µM) |
|---|---|
| 9 | 0.045 |
| 10 | 0.13 |
| 11 | 0.118 |

-continued

| Example | IC$_{50}$ (µM) |
|---|---|
| 19 | 0.048 |
| 23 | 0.086 |

Growth of Human Xenografts from Leiomyoma Tissue in Immunodeficient Mice

The growth-inhibiting action of inhibitors of the androgen receptor was tested in a xenograft animal model with subcutaneously transplanted tissue fragments from human leiomyomas.

Human uterine leiomyoma tissue was derived from surgery, in which, based on the diagnosis, either a hysterectomy or a myomectomy was carried out. The uterine leiomyomas (UL) were then prepared free either from the removed uterus or by myomectomy in situ; in the last-mentioned method, the myomas were removed whole or by morcellation from the abdominal cavity.

The prepared myomas were then immediately put in a suitable sterile buffer (Vitron V7 Buffer (U.S. Pat. No. 5,328,821) or Viaspan organ transplant buffer) at 4° C. for further transport. Then, on a sterile bench with constant moistening, the UL tissue was cut into small blocks with 2×2×2 mm or 2×4×4 mm edge lengths, and the pieces of tissue were stored in a cell culture dish in PBS at room temperature until transplantation (M Fritsch et al. 2010, ISGE abstract & presentation).

Immunodeficient mice (ICR SCID, CB17 SCID, ICR-Hrhr SCID or SCID beige mice) were ovariectomized at the age of 6-8 weeks (OVX). At the earliest one week after OVX, pellets releasing 17β-estradiol (E2, 0.05 mg/90 d, Innovative Research of America, catalogue number NE-121) and progesterone (P, 25 mg/60 d, Innovative Research of America, catalogue number SP-131) (Innovative Research of America, Sarasota, Fla./USA) were transplanted into the neck region of the animals. Alternatively, the animals can be given replacement therapy with other implants or methods that ensure continuous release of the hormones 17β-estradiol and progesterone. These include for example implants based on other matrices, mini-osmotic pumps, or also silicone tubes, filled with hormones and sealed.

Simultaneously with the hormone pellets, the animals each received transplants of eight 2×2×2 mm or four 2×4×4 mm UL pieces of tissue subcutaneously in the abdominal region. The control groups and the treatment groups each received the same number of xenografts per patient. As a rule, 4-5 mice were used per treatment group and tissue from patients.

The wounds were closed after surgery with clips or with an acrylic-based tissue adhesive (Histoacryl, Braun). About 10-14 days after surgery, the mice were divided into two groups. The control group received, once or twice daily by stomach tube, a long-term compatible vehicle that was suitable for the substance in question, e.g. 1% Tylose MH 300/2.5% PEG 400 in water or 10% NMP/90% PEG-300. The treatment group received the test substance once or twice daily in the same vehicle. A typical experimental plan for a UL xenograft experiment was as follows:

| Group | Treatment | Dose mg/kg/d | Duration of treatment | Size of group |
|---|---|---|---|---|
| 1 | E2 0.05 mg/ 90 d pellet | 0.022 | 50 days | 5 mice per donor, 3-5 donors/experiment |
| | P 25 mg/ 60 d pellet | 16.6 | | |
| | Vehicle p.o. | — | | |

-continued

| Group | Treatment | Dose mg/kg/d | Duration of treatment | Size of group |
|---|---|---|---|---|
| 2 | E2 0.05 mg/ 90 d pellet | 0.022 | 50 days | 5 mice per donor, 3-5 donors/experiment (the donors are identical to those in the control group) |
| | P 25 mg/ 60 d pellet | 16.6 | | |
| | Antiandrogen p.o. | X | | |

After a test lasting about 50-60 days, the mice were killed and the UL xenografts were removed and prepared. In the case of compounds with strong action, the test duration could be shortened to 40 days.

UL tissue in situ was as a rule characterized by an excessive synthesis and accumulation of proteins of the extracellular matrix, and by increased cell proliferation. Both led to an increase in the weight or volume of the grafts. With the experimental method described above, there was continued subcutaneous, hormone-dependent growth of the UL xenografts in the mouse, and histologically they had their typical properties stated above (M Fritsch et al. 2010, ISGE abstract & talk). Therefore towards the end of the test, the graft weights were adopted as the primary parameter for evaluating the growth of the xenografts. If specific mechanisms of action of the test substances were known or presumed, in addition the cell proliferation and/or the proportion of the extracellular matrix were determined by histological staining.

Statistical Evaluation of the Experiment

The observed graft weights were assumed to have a lognormal distribution. For determining a treatment effect, the logarithms of the weights were used in a mixed linear model with "treatment" as fixed and "patient" as random effect. In order to describe the correlation between the measurements per mouse, a "compound symmetry" structure was assumed. Degrees of freedom were adjusted for heteroscedasticity and all treatment groups were compared with the UL-xenograft control group by means of a Dunnett's test.

In a simpler evaluation, the graft weights were also assumed to have a lognormal distribution and the logarithms of the weights of the treatment groups were compared with the UL-xenograft control group by means of a Dunnett's test (GraphPadPrism v.5.04).

For the compound according to the invention example 23, the inhibitory effect on the growth of UL xenografts was determined using this assay (see FIG. 1).

FIG. 1 shows significant inhibition of the growth of uterine leiomyoma xenografts with a dosage of 70 mg/kg/d of example 23 in 3 out of 4 independent experiments carried out with leiomyoma tissue from different donors. The average inhibition of the normalized xenograft growth over the transplantation weight on day 0 (shown as dashed line at 40 mg) is −24% for a dose of 25 mg/kg/d of example 23 and −59% for a dose of 70 mg/kg/d.

Myometrium Growth Test in the Ovariectomized, Androgen-Substituted Mouse

The growth-inhibiting action of inhibitors of the androgen receptor is tested in an animal model in ovariectomized (OVX) female mice substituted with dihydrotestosterone (DHT).

The uterine growth test in ovariectomized female rodents substituted with 17β-estradiol, e.g. rats and mice, is an established assay for determining the strength of substances with oestrogen or anti-oestrogen action. However, the myometrium of the uterus is also an androgen-dependent organ. The expression of the androgen receptor, which can be stimulated by oestrogens, has been detected immunohistochemically in the myometrium and in UL (Weihua et al. (2002) Biol. Reprod., 67: 616f; Mertens et al. (2001) Eur J Obstet Gynecol Reprod Biol), and the metabolism of the precursor molecule androstenedione to the active androgens testosterone and dihydrotestosterone (Jasonni et al. (1982) J Steroid Biochem). In the animal model, androgens stimulate the growth of the myometrial layer of the uterus (Mobini Far et al. (2007) Eur J Obstet Gynecol Reprod Biol; Nantermet et al. (2005) Endocrinology), which can be inhibited by administration of antiandrogens. The myometrium growth test can therefore be used as a rapid test for an androgenic/antiandrogenic action of a substance. For this, 4-6 week old female rats or 6-8 week old mice are ovariectomized. At the earliest one week after ovariectomy, the animals received, daily for 7 days, 10 mg/kg dihydrotestosterone in benzylbenzoate/castor oil (1+4) as subcutaneous injection. Simultaneously, over a period of seven days, the animals received the test substances in NMP/PEG-300 1+9 daily per os. At the end of the test the animals are killed, and the weight of the prepared uteri is determined as primary parameter for the growth-stimulating effect of the androgens. In a more detailed histological analysis, additionally the height or area of the myometrium can be determined in histological sections as a parameter for myometrial growth. A test group that was only treated with dihydrotestosterone and the vehicle of the substance p.o. serves as positive control; as negative control, a group that is only treated with the dihydrotestosterone vehicle s.c. and the p.o. vehicle.

For the experiment, a uterus growth test is carried out in 4 week old female rats (strain: Han-Wistar). The animals are ovariectomized, and 1-2 weeks later are treated for seven days with 10 mg/kg DHT and the respective test substance in doses of 20 mg/kg and 50 mg/kg as described above. Then the animals are killed and the uteri are removed and weighed. The uterus weights are normalized relative to the body weight of the animals, with 0% growth corresponding to the relative uterus weight in the control group without dihydrotestosterone and without substance, and 100% growth corresponding to the control group with dihydrotestosterone, but without substance.

The invention claimed is:

1. A compound of formula (I)

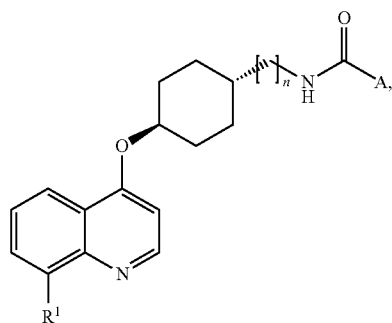

in which

R$^1$ stands for H, cyano, fluorine, chlorine or bromine;
A stands for phenyl or 5-membered heteroaryl, wherein the phenyl or the 5-membered heteroaryl is optionally substituted with one, two or three substituents selected independently of one another from:
halogen, cyano, alkyl-, haloalkyl-, cycloalkyl-, heterocyclyl-, hydroxy, alkoxy-, fluoroalkoxy-, cycloalkyloxy-, amino-, alkylamino-, dialkylamino-, cycloalkylamino-, alkylcycloalkylamino-, dicycloalkylamino-, alkylcarbonylamino-, cycloalkylcarbonylamino-, alkylsulphanyl-, cycloalkylsulphanyl-, alkylsulphonyl-, cycloalkylsulphonyl-, aminosulphonyl-, alkylaminosulphonyl-, cycloalkylaminosulphonyl-; and alkoxycarbonyl-;
n=0, 1 or 2;
or a salt thereof.

2. The compound of claim 1, wherein
R$^1$ stands for H, cyano, fluorine or bromine;
A stands for phenyl or 5-membered heteroaryl, wherein the phenyl or the 5-membered heteroaryl is optionally substituted with one or two substituents selected independently of one another from:
halogen, cyano, alkyl-, and haloalkyl-;
n=0 or 1;
or a salt thereof.

3. The compound of claim 1, wherein
R$^1$ stands for H, bromine, cyano or fluorine;
A stands for phenyl or 5-membered heteroaryl, wherein the phenyl or the 5-membered heteroaryl is optionally substituted with one or two substituents selected independently of one another from: fluorine, chlorine, cyano, methyl and trifluoromethyl;
n=0 or 1;
or a salt thereof.

4. The compound of claim 1 selected from
N-({trans-4-[(8-fluoroquinolin-4-yl)oxy]cyclohexyl}methyl)-4-fluorobenzamide,
N-{trans-4-[(8-bromoquinolin-4-yl)oxy]cyclohexyl}-5-methylisoxazole-3-carboxamide,
N-[trans-4-(4-quinolyloxy)cyclohexyl]-3,4-difluorobenzamide,
N-({trans-4-[(8-fluoroquinolin-4-yl)oxy]cyclohexyl}methyl)-3-methylisoxazole-4-carboxamide,
N-({trans-4-[(8-fluoroquinolin-4-yl)oxy]cyclohexyl}methyl)-isoxazole-5-carboxamide,
N-({trans-4-[(8-fluoroquinolin-4-yl)oxy]cyclohexyl}methyl)isoxazole-3-carboxamide,
N-({trans-4-[(8-fluoroquinolin-4-yl)oxy]cyclohexyl}methyl)-5-methylisoxazole-3-carboxamide,
N-({trans-4-[(8-fluoroquinolin-4-yl)oxy]cyclohexyl}methyl)-1H-pyrazole-3-carboxamide,
N-{[trans-4-(4-quinolyloxy)cyclohexyl]methyl}-3,4-difluorobenzamide,
N-{[trans-4-(4-quinolyloxy)cyclohexyl]methyl}-3-fluorobenzamide,
N-{[trans-4-(4-quinolyloxy)cyclohexyl]methyl}-5-methylisoxazole-3-carboxamide,
N-{trans-4-[(8-bromoquinolin-4-yl)oxy]cyclohexyl}-3-fluorobenzamide,
N-{trans-4-[(8-bromoquinolin-4-yl)oxy]cyclohexyl}-3,4-difluorobenzamide,
N-{trans-4-[(8-bromoquinolin-4-yl)oxy]cyclohexyl}-3-fluoro-4-methylbenzamide,
N-{trans-4-[(8-bromoquinolin-4-yl)oxy]cyclohexyl}-4-cyanobenzamide,
N-{trans-4-[(8-bromoquinolin-4-yl)oxy]cyclohexyl}-3-fluoro-4-(trifluoromethyl)benzamide, N-{trans-4-[(8-bromoquinolin-4-yl)oxy]cyclohexyl}-4-fluorobenzamide, N-{trans-4-[(8-bromoquinolin-4-yl)oxy]cyclohexyl}-3-chloro-4-fluorobenzamide, N-{trans-4-(4-quinolyloxy)cyclohexyl}-3-fluorobenzamide, N-({trans-4-[(8-bromoquinolin-4-yl)oxy]cyclohexy}methyl)-5-methylisoxazole-3-carboxamide, N-({trans-4-[(8-bromoquinolin-4-yl)oxy]cyclohexyl}methyl)isoxazole-3-carboxamide, N-{[trans-4-(4-quinolyloxy)cyclohexyl]methyl}-4-cyanobenzamide N-{trans-4-[(8-cyanoquinolin-4-yl)oxy]cyclohexyl}-3-fluorobenzamide, N-{trans-4-[(8-cyanoquinolin-4-yl)oxy]cyclohexyl}-3,4-difluorobenzamide, N-{trans-4-[(8-cyanoquinolin-4-yl)oxy]cyclohexyl}-4-fluorobenzamide, N-{trans-4-[(8-cyanoquinolin-4-yl)oxy]cyclohexyl}-5-methylisoxazole-3-carboxamide, 3-chloro-N-{trans-4-[(8-cyanoquinolin-4-yl)oxy]cyclohexy}-4-fluorobenzamide, N-{trans-4-[(8-cyanoquinolin-4-yl)oxy]cyclohexyl}-3-fluoro-4-methylbenzamide, 4-chloro-N-{trans-4-[(8-cyanoquinolin-4-yl)oxy]cyclohexyl}-3-fluorobenzamide, N-{trans-4-[(8-cyanoquinolin-4-yl)oxy]cyclohexyl}-3,5-difluorobenzamide, N-({trans-4-[(8-cyanoquinolin-4-yl)oxy]cyclohexyl}methyl)isoxazole-3-carboxamide, and N-({trans-4-[(8-cyanoquinolin-4-yl)oxy]cyclohexyl}methyl)-5-methylisoxazole-3-carboxamide.

5. A method of producing a compound of formula (I) or a salt thereof according to claim 1, comprising reacting a compound of formula (II)

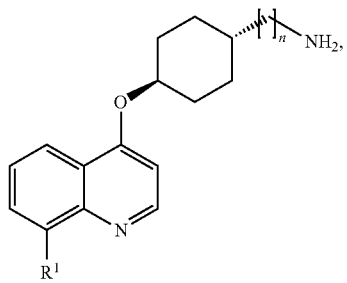

(II)

in which $R^1$ and n have the meaning defined in claim 1, is with an acid chloride A-COCl, in which A has the meaning defined in claim 1, in the presence of a base, and optionally converting the resulting compound of formula (I) with a corresponding (i) solvent and/or (ii) base or acid into a salt thereof.

6. A method of producing a compound of formula (I) or a salt thereof according to claim 1, comprising reacting a compound of formula (II)

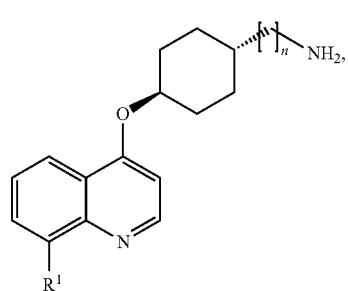

(II)

in which $R^1$ and n have the meaning defined in claim 1, with an acid A-COOH, in which A has the meaning defined in claim 1, in the presence of a suitable coupling reagent and a base, and optionally converting the resulting compound of formula (I) with a corresponding (i) solvent and/or (ii) base or acid into a salt thereof.

7. A method of producing a compound of formula (I) according to claim 1, in which $R^1$=cyano or one of its salts, of its solvates or of the solvates of its salts, comprising submitting a compound of formula (VII)

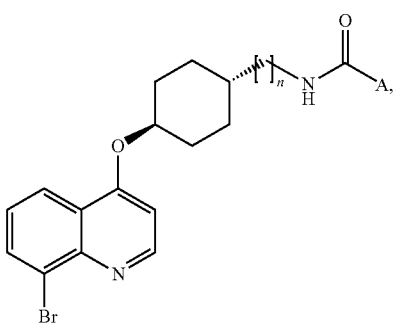

VII in which n and A have the meaning defined in claim 1, are to a bromine/cyano exchange reaction, and optionally converting the resulting compound of formula (I) in which $R^1$=cyano with a corresponding (i) solvent and/or (ii) base or acid into a salt thereof.

8. A method of treatment of a hyperproliferative disease comprising administering to human or animal an effective amount of a compound of claim 1.

9. The method of claim 8, wherein the hyperproliferative disease is an androgen receptor-dependent hyperproliferative disease.

10. A medicinal product comprising the compound of claim 1 and another active substance.

11. A medicinal product comprising the compound of claim 1 and an inert, non-toxic, pharmaceutically suitable excipient.

12. A method of treatment of a hyperproliferative disease comprising administering to a human or animal in need thereof an effective amount of the medicinal product of claim 11.

13. The method of claim 12, wherein the hyperproliferative disease is a androgen receptor-dependent hyperproliferative disease.

14. A compound of formula (II)

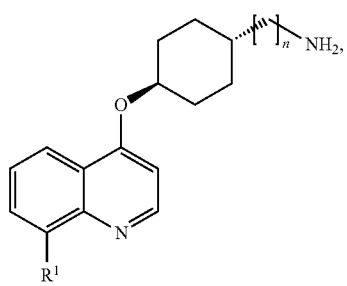

in which R¹ stands for H, cyano, fluorine, chlorine or bromine and n is 0, 1, or 2.

15. The compound of claim 1, in which A stands for isoxazolyl, wherein the isoxazolyl is optionally substituted with a methyl group.

16. The compound of claim 1, in which A stands for phenyl, wherein the phenyl is optionally substituted with a fluoro substituent.

17. The compound of claim 1, in which A stands for fluorophenyl.

18. The compound of claim 1, in which A stands for 3-fluorophenyl.

19. The compound of claim 1, in which R¹ stands for H, cyano, fluorine or bromine.

20. The compound of claim 1, in which R¹ stands for cyano or fluorine.

21. The compound of claim 1, in which R¹ stands for cyano.

22. The compound of claim 1, in which R¹ stands for fluorine.

23. The compound of claim 1, in which n=0 or 1.

* * * * *